United States Patent [19]

Keith et al.

[11] Patent Number: 5,159,077

[45] Date of Patent: Oct. 27, 1992

[54] PENAM ANTIBACTERIAL COMPOUNDS

[75] Inventors: Dennis D. Keith, Montclair; John L. Roberts, Budd Lake; Chung-Chen Wei, Cedar Knolls, all of N.J.

[73] Assignee: Hoffmann-La Roche Inc., Nutley, N.J.

[21] Appl. No.: 383,783

[22] Filed: Jul. 21, 1989

[51] Int. Cl.$^5$ .................... C07D 499/02; A61K 31/43
[52] U.S. Cl. .................... 540/310; 540/222; 540/227
[58] Field of Search ............... 540/310, 312; 514/192, 514/195

[56] References Cited

U.S. PATENT DOCUMENTS

| | | | |
|---|---|---|---|
| Re. 32,491 | 9/1987 | Iwanami et al. | 540/221 |
| 3,971,778 | 7/1976 | Cook et al. | 260/243 C |
| 4,152,432 | 5/1979 | Heymes et al. | 424/246 |
| 4,187,221 | 2/1980 | Micetich et al. | 260/239 A |
| 4,202,893 | 5/1980 | Haynes et al. | 424/246 |
| 4,229,443 | 10/1980 | Binderup | 424/200 |
| 4,259,333 | 3/1981 | Binderup | 501/36 |
| 4,263,432 | 4/1981 | Iwanami et al. | 544/21 |
| 4,278,792 | 7/1981 | Cesti et al. | 542/420 |
| 4,404,373 | 9/1983 | Iwanami et al. | 544/21 |
| 4,431,653 | 2/1984 | Wei et al. | 424/270 |
| 4,476,123 | 10/1984 | Labeeuw et al. | 514/206 |
| 4,604,387 | 8/1986 | Labeeuw et al. | 514/206 |
| 4,647,556 | 3/1987 | Lattrell et al. | 514/206 |
| 4,670,444 | 6/1987 | Grohe et al. | 514/206 |
| 4,753,925 | 6/1988 | Grohe et al. | 514/254 |
| 4,753,953 | 6/1988 | Masuzawa et al. | 514/312 |
| 4,758,567 | 6/1988 | Desideri et al. | 514/254 |
| 4,762,831 | 8/1988 | Grohe et al. | 514/230.2 |
| 4,762,845 | 8/1988 | Chu et al. | 514/312 |
| 4,767,762 | 8/1988 | Chu | 514/254 |
| 4,808,711 | 2/1989 | Shimizu et al. | 540/227 |
| 4,844,902 | 7/1989 | Grohe | 424/449 |
| 4,946,837 | 8/1990 | Miyoke et al. | 514/206 |
| 4,946,847 | 8/1990 | Jolidon et al. | 514/229.5 |

FOREIGN PATENT DOCUMENTS

| | | |
|---|---|---|
| 49891 | 4/1982 | European Pat. Off. |
| 060745 | 9/1982 | European Pat. Off. |
| 148243 | 7/1985 | European Pat. Off. |
| 121244 | 10/1985 | European Pat. Off. |
| 160546 | 11/1985 | European Pat. Off. |
| 187456 | 11/1985 | European Pat. Off. |
| 178980 | 4/1986 | European Pat. Off. |
| 192176 | 8/1986 | European Pat. Off. |
| 036812 | 9/1987 | European Pat. Off. |
| 153709 | 9/1989 | European Pat. Off. |
| 335297 | 10/1989 | European Pat. Off. |
| 366189 | 5/1990 | European Pat. Off. |
| 366193 | 5/1990 | European Pat. Off. |
| 366640 | 5/1990 | European Pat. Off. |
| 366641 | 5/1990 | European Pat. Off. |
| 366643 | 5/1990 | European Pat. Off. |
| 3012667 | 10/1980 | Fed. Rep. of Germany |
| 3233376 | 3/1983 | Fed. Rep. of Germany |
| 2501209 | 9/1982 | France |
| 2007646 | 5/1979 | United Kingdom |
| 1585165 | 2/1981 | United Kingdom |
| 1591439 | 6/1981 | United Kingdom |
| 87/05297 | 9/1987 | World Int. Prop. O. |

OTHER PUBLICATIONS

"Burger's Medicinal Chemistry", Wolff, M. E., ed., Fourth Ed., Part II, pp. 83–85, 100–101, 107–108, 131–136.
Agnew. Chem. Int. Ed. Engl., 24, 180 (1985).
Derwent Abstract of EPA 36 812.
Derwent Abstract of EPA 153 709.
Derwent Abstract of DE 3 233 376.
O'Callaghan et al., Antimicrobial Agents and Chemotherapy, 10(2), 245 (1976).
O'Callaghan et al., J. Bacteriology, 110(3), 988 (1972).
Mobashery et al., J. Amer. Chem. Soc., 108, 1685 (1986).
Mobashery et al., J. Bio. Chem., 261(17), 7879 (1986).
Russell et al., J. Bacteriology, 106(1), 65 (1971).
Decad et al., J. Bacteriology, 128(1), 325 (1976).
Nikaido, "The Role of Outer Membrane Permeability in the Sensitivity and Resistance of Gram-Negative Organisms to Antibiotics", in Drug Resistance in Bacteria, S. Mitsuhnshi (ed.), Thiene-Shetton Inc., N.Y., (1982), 317–324.
Faraci et al., J. Amer. Chem. Soc., 106, 1489 (1989).
Jeffery et al., J. Org. Chem., 47(3), 587 (1982).
Litter, "Framacologia", 6a. Ed. El Ateneo, Buenos Aires, (1980), p. 1517.
Albrecht et al., J. Med. Chem., 33, 77 (1990).
Albrecht et al., J. Med. Chem., 34, 669 (1991).
Albrecht et al., J. Med. Chem., 34, 2857 (1991).

(List continued on next page.)

Primary Examiner—Nicholas S. Rizzo
Attorney, Agent, or Firm—George M. Gould; George W. Johnston; Alan P. Kass

[57] ABSTRACT

Antibacterial compounds of the formula

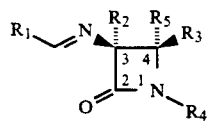

in which
$R_1$ is a cyclic or secondary acyclic amino group which independently has antibacterial activity;
$R_2$ is hydrogen, lower alkoxy, lower alkylthio or formamido;
$R_3$ is hydrogen or an organic group bonded through carbon, oxygen, sulfur or nitrogen;
$R_4$ is an electronegative acidic group; or $R_3$ and $R_4$ together form a heterocycle; and
$R_5$ is a hydrogen or lower alkyl, except when $R_3$ and $R_4$ form a heterocycle, in which case $R_5$ is hydrogen only; and methods of using same.

17 Claims, No Drawings

OTHER PUBLICATIONS

Lund. F. J. "6β-Amidinopenicillanic Acids—Synthesis and Antibacterial Properties", Leo Pharmaceutical Products—Recent Advances in the Chemistry of β-Lactam Antibiotics, pp. 25-27 (England, 1977).

Biochem. J., 116, 371 (1970).

Antimicrobial Agents and Chemotherapy, 10(2), 245 (1976).

Progress in Drug Research, 21, 9, 9 (1977).

The Chemistry and Biology of β-Lactam Antibiotics, vol. 3, App. A, pp. 379-392 (1982).

Antimicrobial Agents and Chemotherapy, 28(4), 581 (1985).

Agnew. Chem. Int. Ed. Engl., 24, 180 (1985).

Annual Reports in Medicinal Chemistry, 20, 145 (1985).

J. Med. Chem., 29(3), 394 (1986).

Annual Reports in Medicinal Chemistry, 21, 139 (1986).

Antimicrobial Agents and Chemotherapy, 31(4), 614 (1987).

American Journal of Medicine, 82, (Suppl. 4A), 12 (Apr. 27, 1989).

J. Antimicrobial Chemotherapy, 17, 5 (1986).

Annual Reports in Medicinal Chemistry, 21, 117 (1987).

Antimicrobial Agents and Chemotherapy, 31(11), 1831 (1987).

Drugs, 34 (Supp. 2), 1 (1987).

J. Med. Chem., 31, 983 (1988).

J. Med. Chem., 31, 991 (1988).

Hackh's Chemistry Dictionary, Grant, J., ed., 3rd Ed., McGraw-Hill, N.Y., p. 814 (1944).

Antimicrobial Agents and Chemotherapy, 10(2), 249 (1976).

J. Med. Chem., 5, 1063 (1962).

*J. Med. Chem.*, 20(6), 791 (1977).

*J. Med. Chem.*, 21(5), 485 (1978).

*J. Med. Chem.*, 23(12), 1358 (1977).

*J. Med. Chem.*, 27(3), 292 (1984).

*J. Med. Chem.*, 27(9), 1103 (1984).

*J. Med. Chem.*, 27(12), 1543 (1984).

*J. Med. Chem.*, 28(11), 1558 (1985).

*J. Med. Chem.*, 29(3), 394 (1986).

*J. Med. Chem.*, 29(4), 445 (1986).

*J. Med. Chem.*, 30(3), 504 (1987).

*Tetrahedron*, 23, 4719 (1967).

*Synthesis*, 787 (1979).

*J. Heterocyclic Chem.*, 22, 1033 (1985).

Derwent Abstract of EPA 060,745.

Derwent Abstract of EPA 178,980.

Heifetz, Carl L. and Domagala, John M., "*The New Generation of Quinolones*", Marcel Dekker, Inc., N.Y., 1990.

Chemical Abstracts, vol. 97, 5572 (1982).

Chemical Abstracts, vol. 98, 125757 (1982).

PENAM ANTIBACTERIAL COMPOUNDS

SUMMARY OF THE INVENTION

The present invention comprises compounds of the formula

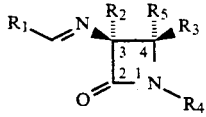

in which $R_1$ is a cyclic or secondary acyclic amino group which independently has antibacterial activity;

$R_2$ is hydrogen, lower alkoxy, lower alkylthio or formamido;

$R_3$ ia hydrogen or an organic group bonded through carbon, oxygen, sulfur or nitrogen;

$R_4$ is an electronegative acidic group; or $R_3$ and $R_4$ together form a heterocycle; and $R_5$ is hydrogen or lower alkyl, except when $R_3$ and $R_4$ form a heterocycle, in which case $R_5$ is hydrogen only.

Also included within the scope of this invention are the corresponding readily hydrolyzable esters, pharmaceutically acceptable salts and hydrates of any of the foregoing.

These compounds are useful as antibacterial agents, for both prophylactic and therapeutic purposes.

Pharmaceutical compositions containing an antibacterial amount of such compounds and the combatting of bacterial infections in a host by the administration of an effective amount of such compounds constitute additional aspects of this invention.

DETAILED DESCRIPTION OF THE INVENTION

Listed below are the definitions of various terms used in this disclosure. These definitions apply throughout the specification unless otherwise stated.

The terms "alkyl" and "lower alkyl" refer to both straight and branched chain, saturated hydrocarbon groups having from 1 to 7, preferably from 1 to 4, carbon atoms; for example, methyl, ethyl, propyl, isopropyl, tertiary butyl, and the like.

The terms "lower alkoxy" and "alkoxy" refer to a straight or branched chain hydrocarbonoxy group wherein the alkyl portion is an alkyl group as defined above. Examples include methoxy, ethoxy, propoxy, and the like.

The terms "alkanoyl", "alkenyl" and "alkynyl" refer to both straight and branched chain groups. Preferred are those having from 2 to 8 carbon atoms.

The terms "halogen" or "halo" wherever used herein refer to chloro, bromo, iodo and fluoro.

The term "electronegative acidic group" refers to acidic groups capable of forming a negatively charged radical.

The term "aryl" refers to phenyl and phenyl substituted with 1, 2 or 3 amino, halogen, hydroxyl, trifluoromethyl, alkyl, alkoxy or carboxy groups.

The term "heteroaryl" refers to those 5-, 6- or 7-membered heterocycles which are aromatic.

The expression "5-, 6-, or 7-membered heterocycle" refers to substituted and unsubstituted, aromatic and non-aromatic groups containing one or more, preferably one or two, heteroatoms selected from the group consisting of nitrogen, oxygen and sulfur. Exemplary substituents are oxo (=O), halogen, hydroxy, nitro, amino, cyano, trifluoromethyl, alkyl, alkoxy, alkylsulfonyl, phenyl, substituted phenyl, etc. The non-aromatic heterocycles may be fully saturated or partially saturated. Examples of non-aromatic heterocycles are substituted and unsubstituted piperidinyl, piperazinyl, imidazolidinyl, oxazolidinyl, pyrrolidinyl, tetrahydropyrimidinyl, and dihydrothiazolyl. Examples of the substituted 5-, 6-, or 7-membered heterocycles are 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-aryl-2-oxo-1-imidazolidinyl, 3-(2-hydroxyethyl)-2-oxo-1-imidazolidinyl, 3-[(1-methylethylidene)amino]-2-oxo-1-imidazolidinyl, 3-benzyl-2-oxo-1-imidazolidinyl, 3-(2-aminoethyl)-2-oxo-1-imidazolidinyl, 3-[(2-alkylamino)ethyl]-2-oxo-1-imidazolidinyl, 3-[(2-dialkylamino)ethyl]-2-oxo-1-imidazolidinyl, 3-amino-2-oxo-1-imidazolidinyl, 3-ureido-2-oxo-1-imidazolidinyl, 3-[(alkoxycarbonyl)-amino]-2-oxo-1-imidazolidinyl, 3-[2-alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyriumidinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl. Examples of aromatic heterocycles (heteroaryl group) are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl and tetrazolyl.

The term "substituted alkyl" refers to alkyl groups substituted with one or more azido, amino, halogen, hydroxy, carboxy, cyano, alkoxycarbonyl, aminocarbonyl, alkanoyloxy, alkoxy, aryloxy, mercapto, alkylthio, arylthio, alkylsulfinyl, or alkylsulfonyl groups.

The expression "5- or 6-membered heterocyclic ring containing 1 or 2 heteroatoms selected from the group consisting of oxygen, nitrogen, and sulfur" is intended to represent the following ring systems commonly found in bicyclic beta-lactam antibiotics (the term "antibiotic" being used in this disclosure interchangeably with the term antibacterial agent): namely, thiazolidine (penams), 2,3-dihydrothiazole (penems), 2,3-dihydropyrrole (carbapenems), 2,3-dihydro-1,3-thiazine (cephalosporins), 2,3-dihydro-1,3-oxazine (oxacephalosporins), and 1,2,3,4-tetrahydropyridine (carbacephalosporins). Each of these heterocyclic rings may be further substituted in the manner of conventional beta-lactam antibiotics as exemplified in the art; see, for example, Recent Advances in the Chemistry of Beta-Lactam Antibiotics, ed. J. Elks, Royal Society of Chemistry, London (1977); Recent Advances in the Chemistry of Beta-Lactam Antibiotics-Second International Symposium-1980, ed. G. I. Gregory, Royal Society of Chemistry, London (1981); Recent Advances in the Chemistry of Beta-Lactam Antibiotics-Third International Symposium-1984, ed. A. G. Brown and S. M. Roberts, Royal Society of Chemistry, London (1985); Recent Advances in the Chemistry of Beta-Lactam Antibiotics-Fourth International Symposium-1988, ed. P. H. Bentley and R. Southgate, Royal Society of Chemistry, London (1989); Chemistry and Biology of Beta-Lactam Antibiotics, Vols, 1-3, ed. R. B. Morin and M. Gorman, Academic Press, New York (1982); Cephalosporins and Penicillins. Chemistry and Biology, ed. E. H. Flynn, Academic Press, New York (1972); Beta-Lactam Antibiotics Mode of Action, New Developments and Future Prospects, ed. M. R. J. Salton and G. D. Shockman, Academic Press, New York (1981); Beta-Lactam Antibiotics for Clinical Use, ed. S. F. Queener, S. W. Queener and J. A. Webber, Marcel Dekker, Inc., New York (1986).

Preferred compounds of formula I are those having the following features:

$R_1$, $R_2$ and $R_5$ are as defined previously:

$R_3$ is hydrogen, alkyl, alkenyl, alkynyl, aryl, a 5-, 6-, or 7-membered heterocycle, azido, halomethyl, dihalomethyl, trihalomethyl, alkoxycarbonyl, aminocarbonyl,

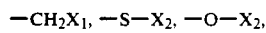

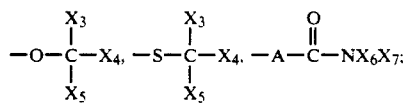

$X_1$ is azido, amino, hydroxy, alkanoylamino, alkylsulfonyloxy, arylsulfonyloxy, aryl, cyano, $-S-X_2$, or $-O-X_2$;

$X_2$ is alkyl, substituted alkyl, aryl, arylalkyl, alkanoyl, substituted alkanoyl, arylcarbonyl, or heteroarylcarbonyl;

$X_3$ is hydrogen and $X_4$ is hydrogen or alkyl; or $X_3$ and $X_4$ when taken together with the carbon to which they are attached form a cycloalkyl ring;

$X_5$ is formyl, alkanoyl, arylcarbonyl, arylalkylcarbonyl, carboxyl, alkoxycarbonyl, aminocarbonyl, (substituted amino)carbonyl, or cyano;

A is $-CH=CH-$, $-CH_2-CH=CH-$, $-(CH_2)_m-$, $-(CH_2)_n-O-$, $-(CH_2)_n-NH-$, $-(CH_2)_n-S-CH_2-$, or $-(CH_2)_n-O-CH_2-$;

$m = 0, 1, 2$ or $3$;

$n = 1$ or $2$;

$X_6$ and $X_7$ are the same or different and each is hydrogen or alkyl, or $X_6$ is hydrogen and $X_7$ is amino, substituted amino, acylamino or alkoxy;

$R_4$ is $-SO_3H$, $-PO_3H$, $-PO_2HOR$, $-PO_2HNHX_4$, $-CH_2CO_2H$, $-OSO_3H$, $-OPO_3H$, $-OCH_2CO_2H$, $-CONHSO_2NX_4X_8$, $-CONHSO_2X_8$, and $-SO_2NHCOX_3$;

$X_3$ and $X_4$ are as described above; and $X_8$ is hydrogen, alkyl, aryl or a 5-, 6- or 7-membered heterocycle; or $R_3$ and $R_4$ together form a carboxylic acid-substituted 5- or 6-membered heterocyclic ring containing 1 or 2 hetero (non-carbon) atoms selected from the group consisting of oxygen, sulfur and nitrogen, provided that if there is only one hetero atom in the ring it must be nitrogen.

Especially preferred compounds in accordance with this invention are those of the formula

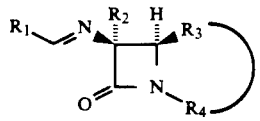 IA in which

represent either of the following

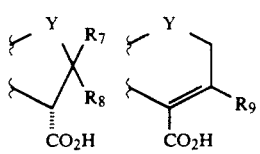

in which Y is O, S or C; $R_7$ and $R_8$ are independently hydrogen or lower alkyl, $R_9$ is hydrogen, halogen, alkenyl, substituted alkenyl of $CH_2X$; and X is hydrogen, $-OCOCH_3$, or a 5- or 6-membered heterocycle linked via a hetereoatom selected from O, S, N or any other group found in that position in cephalosporin chemistry.

In preferred antibacterial compounds of formula I according to this invention, $R_1$ is of the formula

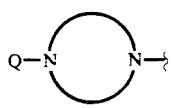

or the formula

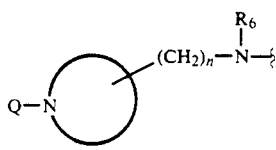

or the formula

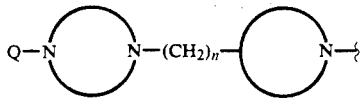

in which

represents a 5-, 6- or 7-membered ring, substituted or unsubstituted,

represents a 5- or 6-membered ring, substituted or unsubstituted, $R_6$ is lower alkyl or substituted lower alkyl, Q represents a substituted quinolinyl or naphthyridinyl group, and n is zero, 1 or 2.

In especially preferred embodiments, as illustrated in the working examples, $R_1$ is a substituted piperazinyl group of the formula

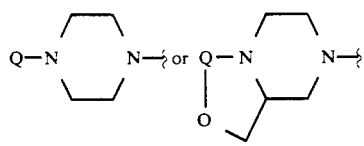

or a substituted diazepinyl group of the formula

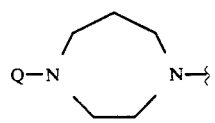

or a substituted pyrrolidinylamino group of the formula

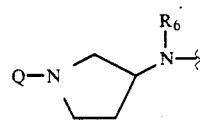

or a substituted pyrrolidinylmethylamino group of the formula

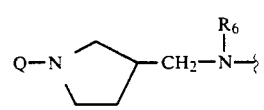

in which Q is defined as above, the piperzine, pyrrolidine and diazepine nuclei may be optionally substituted with one or more lower alkyl or substituted lower alkyl groups, and $R_6$ is a lower alkyl or substituted lower alkyl group.

By way of illustration, $R_1$ includes, among others, compounds of the following formulas:

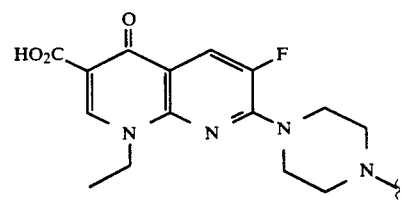

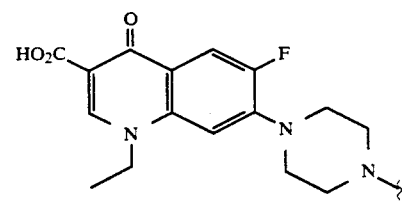

-continued

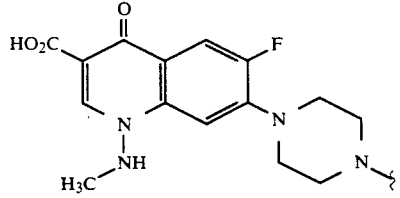

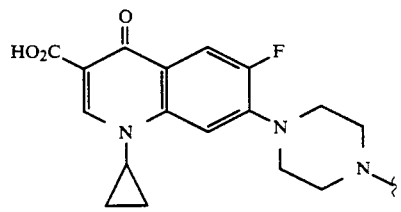

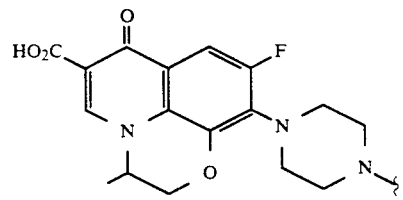

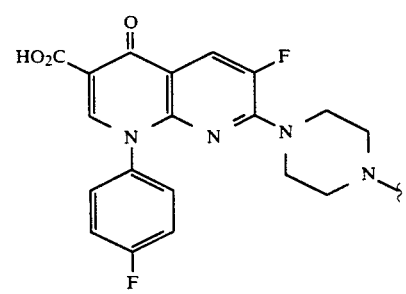

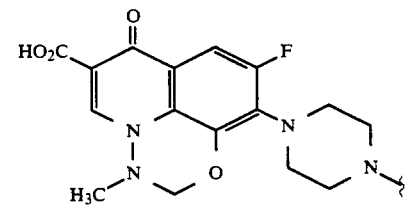

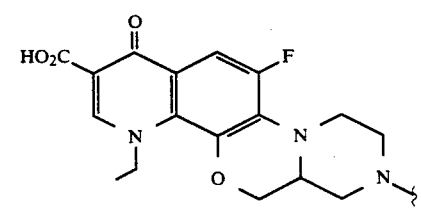

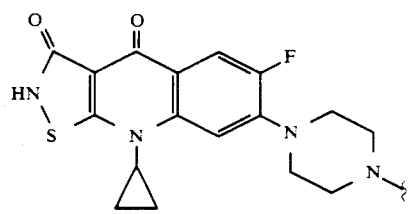
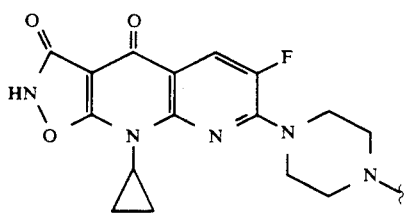
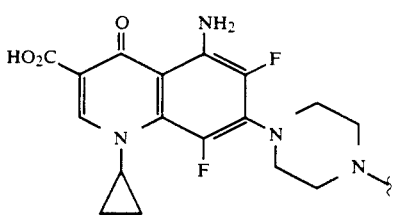
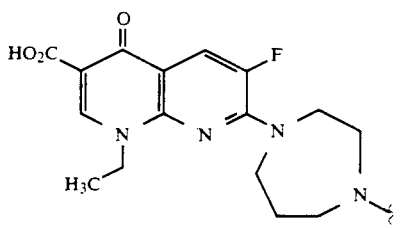
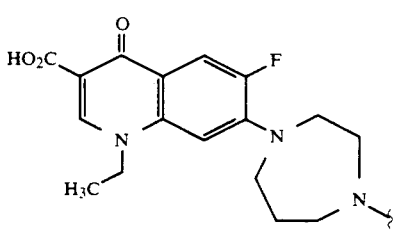
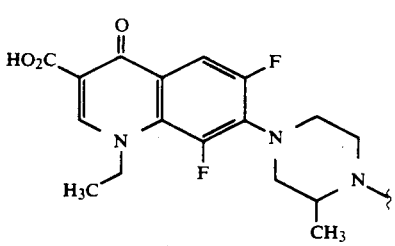
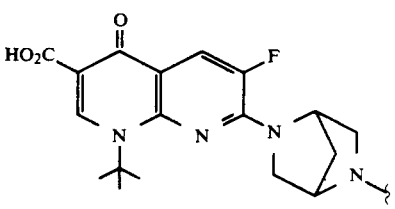

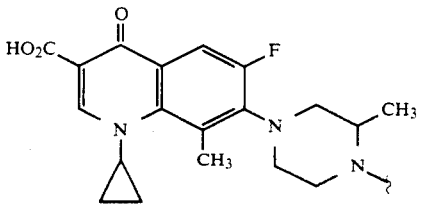
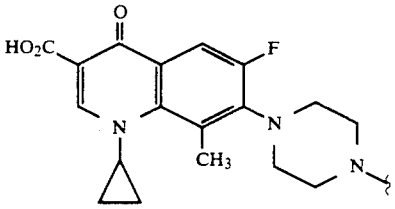
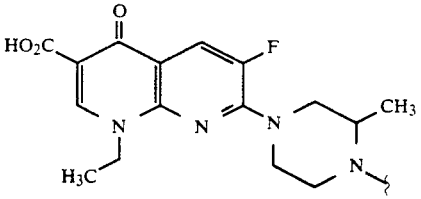

As readily hydrolyzable esters of the compounds of formula I there are to be understood compounds of formula I, the carboxy group(s) of which is/are present in the form of readily hydrolyzable ester groups. Examples of such esters, which can be of the conventional type, are the lower alkanoyloxyalkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used.

Examples of salts of the compounds of formula I are alkali metal salts such as the sodium and potassium salt, the ammonium salt, alkaline earth metal salts such as the calcium salt, salts with organic bases such as salts with amines (e.g., salts with N-ethyl-piperidine, procaine, dibenzylamine, N,N'-dibenzylethylenediamine, alkylamines or dialkylamines), as well as salts with amino acids such as, for example, salts with arginine or lysine.

The compounds of formula I as well as their salts and readily hydrolyzable esters can be hydrates. The hydration can be effected in the course of the manufacturing process or can occur gradually as a result of hygroscopic properties of an initially anhydrous product.

A preferred class of compounds according to this invention are those of the formula

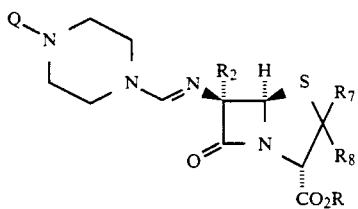

II in which $R_2$ and Q are as defined above, $R_7$ and $R_8$ are independently hydrogen or lower alkyl, and R is hydrogen or a metal cation.

Also preferred are compounds of the formula

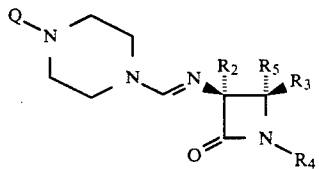

III in which $R_2$, $R_3$, $R_4$, $R_5$ and Q are as previously defined.

Additionally preferred are compounds of the formula

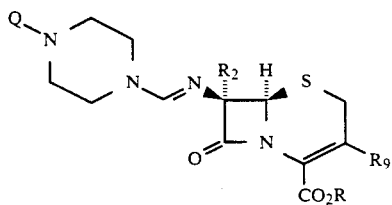

IV in which R, $R_2$, $R_9$ and Q are as defined above.

In the compounds of formulas II, III and IV, Q is preferably of the formula

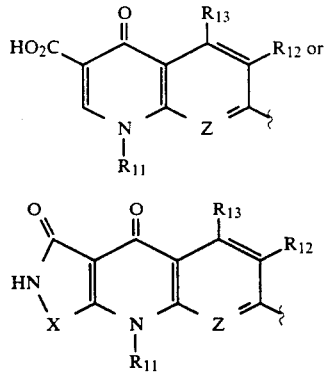

in which Z represents C—$R_{10}$ or N; Z represents S or O; $R_{10}$ represents hydrogen, halogen or an oxymethylene (—$CH_2O$—) bridge to the piperazine nucleus to form a fused six-membered ring; alternatively, $R_{10}$ may be an oxymethylene bridge to the first atom of the N-substituent so as to form a fused six-membered ring; $R_{11}$ represents hydrogen, lower alkyl, lower alkenyl, $C_3$ to $C_7$ cycloalkyl, substituted lower alkyl (preferably halo substituted), or mono-, di-, or trihalophenyl; $R_{10}$ and $R_{11}$ when taken together represent lower alkylene of 3 to 5 carbon atoms, a lower alkylene mono-oxy group of 2 to 4 carbon atoms, or a group of the formula —$OCH_2N(CH_3)$—; $R_{12}$ is hydrogen or halogen; and $R_{13}$ is hydrogen or amino.

In the most preferred embodiments, Z is N or C—$R_{10}$ in which $R_{10}$ is hydrogen, chloride, bromine, fluorine or an oxymethylene bridge; $R_{11}$ is lower alkyl, especially ethyl, or halogen lower alkyl, especially fluoroethyl; and $R_{12}$ is hydrogen, chlorine or fluorine, especially fluorine.

The compounds of this invention can be used as agents to combat bacterial infections in mammalian species, for example, dogs, cats, etc., and humans.

The in vitro activity of the compounds of this invention as measured by the Minimum Inhibitory Concentration (MIC) in micrograms per milliliter (mcg/ml) against various bacterial microorganisms, utilizing the Broth Dilution Method and the Agar Well Diffusion Method, is demonstrated as follows:

Compound A: [2S-(2α,5α,6β)]-6-fluoro-1,4-dihydro-3-(methoxycarbonyl)-4-oxo-7-quinolinyl]-1-piperazinyl]methylene]amino]-3,3-dimethyl-6-oxo-4-thia-1-azabicyclo[3.2.0]heptane -2-carboxylic acid Compound B: [2S-(2α,5α,6β)]-7-[4-[[[2-(Carboxy)-3,3-dimethyl-7-oxo-4-thia-1-azabicyclo[3.2.0]hept-6-yl]imino]methyl]-1-piperazinyl]-1-ethyl-6-fluoro-1,4-dihydro-4-oxo-3-quinolinecarboxylic acid monosodium salt Compound C: 6R-[6α,7β(E()]-7-[4-[[(2-Carboxy-3-methyl-8-oxo-5-thia-1-azabicyclo[4.2.0]oct-2-en-7-yl)imino]-methyl]-1-piperazinyl]-1-ethyl-6-fluoro-1,4-dihydro-4-oxo-3-quinolinecarboxylic acid disodium salt Compound D: 2R-(2α,5α,6β)]-7-[4-[[(2-Carboxy-3,3-dimethyl-7-oxo-4-thia-1-azabicyclo[3.2.0]hept-6-yl)amino]-methylene]-1-piperazinyl]-6,8-difluoro-1-(2-fluoroethyl)-1,4-dihydro-4-dihydro-4-oxo-3-quinoline-carboxylic acid monosodium salt Compound E: (S)-1-Ethyl-6-fluoro-1,4-dihydro-4-oxo-7-[4-[[(1-sulfo-2-oxo-3-azetidinyl)imino]methyl]-1-piperazinyl]-3-quinolinecarboxylic acid disodium salt Compound F: (2S-cis)-7-[4-[[[2-[[(Aminocarbonyl)oxy]-methyl]-4-oxo-1-sulfo-3-azetidinyl]imino]methyl]-1-piperazinyl]-1-ethyl-6-fluoro-1,4-dihydro-4-oxo-3-quinolinecarboxylic acid disodium salt Compound G: [2S-(2α,5α,6β)]-7-[4-[[)2-Carboxy-3,3-dimethyl-7-oxo-4-thia-1-azabicyclo[3.2.0]hept-6-yl)-imino]methyl]hexahydro-1H-1,4-diazepin-1-yl]-1-ethyl-6-fluoro-1,4-dihydro-4-oxo-3-quinolinecarboxylic acid disodium salt Compound H: [2S-(2α,5α,6β]-7-[4-[[(2-Carboxy-2,3-dimethyl-7-oxo-4-thia-1-azabicyclo[3.2.0]-hept-6-yl)imino]methyl]-1-piperazinyl]-1-ethyl-6-fluoro-1,4-dihydro-4-oxo-1,8-naphthyridinecarboxylic acid disodium salt Compound I: [6R-[6α,7β(Z)]]-7-[4-[[[3-[Acetyloxy)methyl]-2-carboxylic-8-oxo-5-thia-1-azabicyclo[4..-0]oct-2-en-7-yl]imino]methyl]-1-piperazinyl]-1-ethyl-6-fluoro-1,4-dihydro-4-oxo-3-quinolinecarboxylic acid monosodium salt Compound J: [6R-[6α,7β(Z)]]-7-[4-[[[2-Carboxy-3-[[(1,2,5,6-tetrahydro-2-methyl-5,6-dioxo-1,2,4-triazin-3-yl)thio]methyl]-8-oxo-5-thia-1-azabicyclo[4.2.0]-oct-2-en-7-yl]-imino]methyl]-1-piperazinyl]-ethyl-6-fluoro-1,4-dihydro-4-oxo-3-quinolinecarboxylic acid disodium salt Compound K: [2S-(2α,5α,6β)]-7-[4-[[2-Carboxy-3,3-dimethyl-7-oxo-4-thia-1-azabicyclo[3.2.0]hept-6-yl)- imino]methyl]hexahydro-1H,
1,4-diazepin-1-yl]-1-ethyl-6-fluoro-1,4-dihydro-4-oxo-1,8-naphthyridine--carboxylic acid disodium salt.

Broth Dilution Method

The diluted agents prepared in Mueller-Hinton broth were dispensed from a Dynatech MIC 2000 machine, in 100 microliter ($\mu$L) volumes into 96 well trays and used immediately or frozen at $-10°$ to $-70°$ C. until needed. Using a Dynatech inoculator and inoculum trays, 1.5 $\mu$L of a $10^{-2}$ dilution of an overnight culture was added to each well of the tray. The tops of the trays were then sealed with tape, and the trays were incubated overnight at 37° C. and then examined with a viewer. The lowest concentration at which no growth was observed was considered to be the minimum inhibitory concentration (MIC).

Agar Well Diffusion Method

In vitro antimicrobial activity was determined in BBL seed agar. Serial dilutions of the test compound were pipetted into agar wells (80 $\mu$L per well). After incubation, the lowest concentration of compound which showed a zone of inhibition was designated the "minimum inhibitory concentration". For reference, see A. H. Litton, Antibiotics: Assessment of Antimicrobial Activity and Resistance, Academic Press, New York, pages 19-30 (1983).

illustration, such methods of administration include parenteral, for example, intravenous or intramuscular, and enteral, for example, as a suppository.

The following reaction schemes set forth the methods and intermediates useful in producing the end products of formula I. Unless otherwise noted, $R_2$, $R_3$, $R_4$, $R_5$ and Q are as previously defined.

SCHEME 1

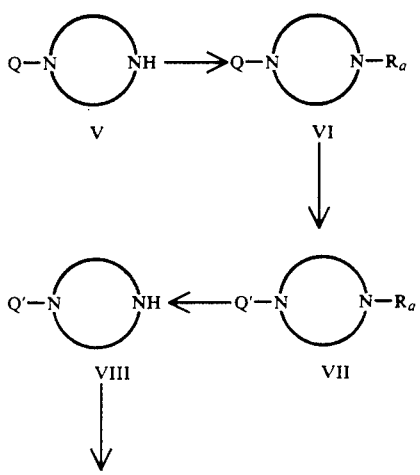

TABLE 1

| Microorganism/Compound | In Vitro MIC (mcg/ml), Broth Dilution Method ||||||||||| 
| | A | B | C | D | E | F | G | H | I | J | K |
| --- | --- | --- | --- | --- | --- | --- | --- | --- | --- | --- | --- |
| *Escherichia coli* 4 | 8 | 0.5 | 0.125 | 0.125 | 0.125 | 0.125 | 2 | 0.125 | 0.125 | 0.25 | 2 |
| *Escherichia coli* TEM-1 | 4 | 0.031 | 0.063 | 0.125 | 0.063 | 0.063 | 1 | 0.125 | 0.063 | 0.25 | 1 |
| *Klebsiella pneumoniae* A | 16 | 0.125 | 0.125 | 0.125 | 0.125 | 0.125 | 2 | 0.25 | 0.125 | 0.5 | 2 |
| *Enterobacter cloacae* 5699 | 8 | 0.063 | 0.063 | 0.25 | 0.125 | 0.063 | 2 | 0.125 | 0.125 | 0.25 | 4 |
| *Enterobacter cloacae* P99 | 8 | 0.063 | 0.125 | 0.125 | 0.063 | 0.125 | 2 | 0.125 | 0.063 | 0.5 | 1 |
| *Citrobacter freundii* BS-16 | 32 | 0.25 | 0.25 | 1 | 0.25 | 0.25 | 8 | 0.5 | 0.25 | 0.5 | 4 |
| *Proteus vulgaris* ATCC 6380 | 4 | 0.063 | 0.063 | 0.063 | 0.031 | 0.031 | 1 | 0.125 | 0.063 | 0.125 | 2 |
| *Proteus mirabilis* 2 | 8 | 0.125 | 0.063 | 0.125 | 0.063 | 0.063 | 4 | 0.5 | 0.063 | 0.5 | 4 |
| *Proteus mirabilis* 90 | 32 | 0.5 | 0.25 | 1 | 0.063 | 0.25 | 8 | 1 | 0.5 | 1 | 8 |
| *Serratia marcescens* SM | 16 | 0.125 | 0.125 | 0.25 | 0.063 | 0.063 | 2 | 0.5 | 0.125 | 0.5 | 4 |
| *Pseudomonas aeruginosa* Stone 130 | 64 | 0.5 | 0.5 | 4 | 1 | 0.5 | 8 | 1 | 1 | 8 | 8 |
| *Pseudomonas aeruginosa* ATCC 27853 | >128 | 8 | 2 | 2 | — | 2 | 16 | 8 | 8 | 16 | — |
| *Streptococcus pneumoniae* 6301 | 1 | 0.5 | 8 | 2 | 8 | 8 | 2 | 2 | 0.5 | 2 | 2 |
| *Streptococcus faecalis* ATCC 29212 | 32 | 2 | 8 | 32 | 8 | 4 | 64 | 8 | 4 | 0.25 | 128 |
| *Staphylococcus aureus* Smith | 2 | 0.25 | 0.5 | 0.5 | 0.5 | 0.5 | 2 | 0.5 | 0.25 | 1 | 2 |
| *Staphylococcus aureus* ATCC 29213 | 16 | 0.5 | 1 | 4 | 2 | 2 | 16 | 0.5 | 2 | 2 | 16 |

TABLE 2

| Microorganism/Compound | In Vitro MIC (mcg/ml), Agar Well Diffusion Method ||||||||
| | A | B | C | D | E | F | G | H |
| --- | --- | --- | --- | --- | --- | --- | --- | --- |
| *Pseudomonas aeruginosa* 56 | 500 | 7.8 | 3.9 | 7.8 | 7.8 | 7.8 | 100 | 15.6 |
| *Pseudomonas aeruginosa* B | 250 | 7.8 | 3.9 | 15.6 | 3.9 | 7.8 | 50 | 15.6 |
| *Proteus vulgaris* 101N | 62.5 | 1.95 | 0.98 | 1.95 | 1.95 | 1.95 | 50 | 7.8 |
| *Escherichia coli* 1269B | 62.5 | 0.98 | 3.9 | 1.95 | 7.8 | 7.8 | 50 | 7.8 |
| *Klebsiella pneumoniae* 369 | 125 | 3.9 | 3.9 | 7.8 | 3.9 | 3.9 | 100 | 7.8 |
| *Serratia marcescens* SM | 250 | 62.5 | 3.9 | 31.3 | 3.9 | 62.5 | 50 | 31.3 |
| *Enterobacter cloacae* 2952B | 62.5 | 15.6 | 7.8 | 7.8 | 31.3 | 31.3 | 100 | 31.3 |
| *Streptococcus faecium* ATCC 8043 | 250 | 62.5 | 500 | 15.6 | >125 | 500 | >400 | 125 |
| *Streptococcus aureus* 82 | 7.8 | 7.8 | 15.6 | 3.9 | 15.6 | 31.3 | 50 | 7.8 |
| *Micrococcus luteus* PCl | 31.3 | 31.3 | 250 | 15.6 | >125 | 500 | 25 | 31.3 |

For combatting bacterial infections in mammals, a therapeutically active compound of formula I can be administered to a mammal in an amount of about 5 mg/kg/day to about 500 mg/kg/day, preferably about 10 mg/kg/day to 100 mg/kg/day, and most especially about 10 mg/kg/day to about 55 mg/kg/day.

Modes of administration which have been used in the past to deliver penicillin and cephalosporin antibiotics to the site of infection are also contemplated. By way of

-continued
SCHEME 1

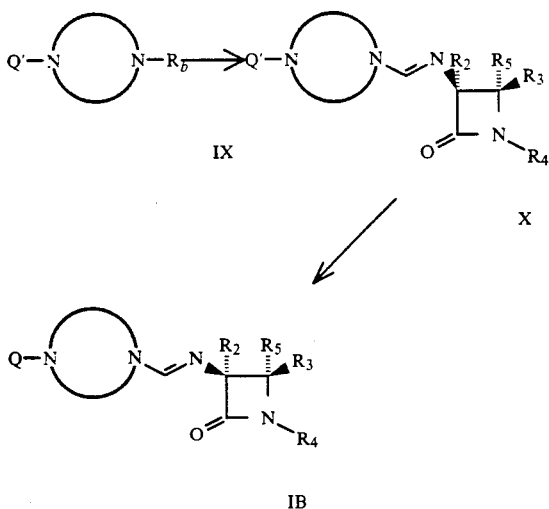

$R_a$ is a readily removable amino nitrogen-protecting group $R_b$ is a masked carbonyl activating group required for amidino formation, e.g., dialkylacetal.

Q' is an ester derivative of Q

Scheme 1

V→I

The compound of formula V is selectively protected on the secondary nitrogen with a readily removable protecting group, Ra, such as those commonly used in peptide chemistry. Examples of types of protecting groups that can be used are alkoxycarbonyl (e.g., tert-butyloxycarbonyl, and the like), substituted alkoxycarbonyl (e.g., 2,2,2-trichloroethoxycarbonyl, and the like), aralkoxycarbonyl and substituted aralkoxycarbonyl (e.g., p-nitrobenzyloxycarbonyl, and the like), or an aralkyl group (e.g., triphenylmethyl). The actual choice of the nitrogen protecting group must be such as to be stable to the esterification conditions required in the next step, but be readily removable after esterification without affecting the newly formed ester function. A preferred protecting group for the secondary nitrogen in the compound of formula V is the tert-butyloxycarbonyl (t-BOC) group. For example, reaction of V with di-tert-butyl dicarbonate gives the compound of formula VI, in which the nitrogen is protected with the tert-butyloxycarbonyl group.

VI→VII→VIII

Compound VI is then protected on the quinoline carboxylic acid group, Q', with a readily removable protecting group such as those typically found in peptide and β-lactam chemistry. As an example, one may utilize an ester function which can be readily converted back to the carboxylic acid under mild conditions. Esterification of compound VI by methods known in the art provides compound VII. The ester group can be, for example, tert-butyl, p-nitrobenzyl, benzhydryl, allyl, 2,2,2-trichloroethyl, 2-trimethylsilylethyl, etc. The preferred choice of ester function is one which is stable to the conditions required to deprotect the protected secondary nitrogen in compound VII, but which can be removed readily under conditions mild enough so as not to disrupt the β-lactam ring or the amidino moiety in compound X. A preferred carboxylic acid protecting group is the p-nitrobenzyl group. Thus, treatment of compound VI, preferably protected with a t-BOC group, with a base yields the corresponding carboxylic acid salt of the base. A preferred base is sodium hydroxide, which gives the corresponding sodium salt of compound VI. This salt is then treated in an organic solvent, preferably dimethylformamide, with p-nitrobenzyl bromide and the mixture is stirred at ambient temperature for three days to give the compound of formula VII. The amine nitrogen-protecting group is then removed by a method known in the art that will leave the ester function intact. In the case of t-BOC protection and a p-nitrobenzyl ester function, for example, the preferred method of removal of the t-BOC protecting group is treatment with trifluoroacetic acid and anisole, to give the compound of formula VIII.

VIII→IX

The compound of formula VIII is then reacted at the secondary nitrogen atom to convert it to the corresponding N-formyl dialkyl acetal, formula IX, which is required for subsequent amidine formation. This is accomplished by treatment of compound VIII with dimethylformamide dialkyl acetal. The alkyl group can be lower alkyl, or branched alkyl. Preferably, if the quinolone ester is formed from a lower alkyl or branched alkyl group, then this alkyl group should be the same one found in the dimethylformamide dialkyl acetal. Thus, for a quinolone methyl ester, dimethylformamide dimethyl acetal is the preferred reagent. For other ester groups the preferred reagent for this transformation is dimethylformamide dineopentyl acetal. Thus, treatment of the quinolone ester of formula VIII with dimethylformamide dineopentyl acetal in anhydrous chloroform as the preferred solvent, and preferably under conditions of reflux for from 5 to 15 hours, yields the compound of formula IX.

IX→X

Reaction of the compound of formula IX with a β-lactam of the formula

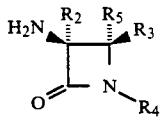

In the presence of a base such as triethylamine or diisopropylethylamine, in an organic solvent such as dichloromethane, chloroform or acetonitrile, at ambient temperature for about 2 to 10 hours, gives the amidino compound of formula X. The base is required to neutralize any acidic functionality in $R_3$ and/or $R_4$. If any acidic function contained in $R_3$ and/or $R_4$ has been selectively blocked with a readily removable protecting group by methods known in the art, then the base may be omitted. For example, reaction of the compound of formula IX with 6-aminopenicillanic acid and diisopropylamine in chloroform for about 2 to 10 hours results in the compound of formula X in which $R_2$ and $R_5$ are hydrogen and $R_3$ and $R_4$ together form the thiazolidine ring of a penam. Compound X, if it contains a free acidic function, may be isolated as the free acid or as a salt by standard methods known in the art. For instance, with 6-aminopenicillanic acid, addition of the sodium salt of 2-ethylhexanoic acid to the reaction during workup gives the corresponding compound of formula X as the sodium salt.

X→IB

In the final step in Scheme 1, the quinolone ester (protected) function, Q' is converted into the free carboxylic acid (deprotected) according to the methods known in the art that will not affect the β-lactam ring and the amidino function. Additionally, if an acidic function in $R_3$ and/or $R_4$ is present in a protected form it can also be deprotected at this point by methods known in the art which are compatible with the preceding criteria. For example, in the case of compound X containing the preferred p-nitrobenzyl ester function, the free carboxylic acid can be generated by a catalytic hydrogenation process. This is preferably carried out at atmospheric pressure with a supported catalyst, such as palladium-on-carbon, in an appropriate solvent compatible with the process, such as aqueous-tetrahydrofuran, to give the compound of formula IB.

SCHEME 2

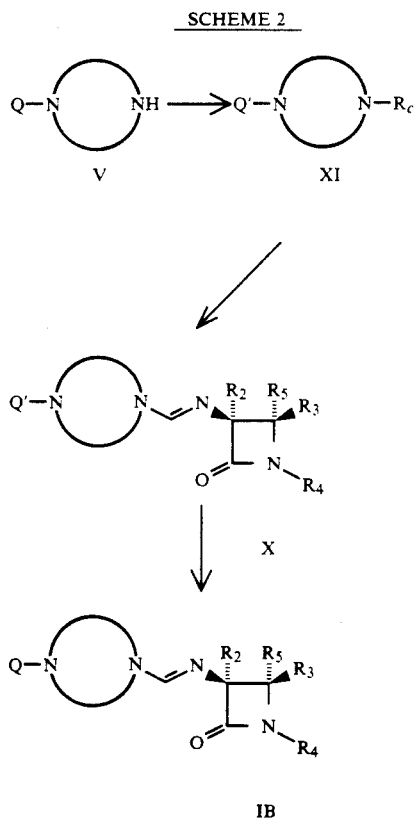

$R_c$ represents an acetal function
Q' is a salt derivative of Q

Scheme 2

V→XI

The compound of formula V, as previously defined, is converted into a salt of the free carboxylic acid by treatment with an appropriate base, using methods known in the art. The choice of base is such as to render the salt soluble in organic solvents. The preferred soluble salt of compound V is a tetra-alkyl ammonium salt, such as tetra-n-butyl ammonium salt. Thus, for example, treatment of the compound of formula V containing a free carboxylic acid group, with tetra-n-butyl ammonium hydroxide, results in the corresponding tetra-n-butylammonium salt, Q'. Alternatively, the same salt may be obtained by treatment of the corresponding sodium salt with tetra-n-butylammonium bisulfate. The resulting organic solvent-soluble quinolone salt is then converted into the N-formyl dialkyl acetal-functionalized quinolone of formula XI. This is accomplished by treatment of the organic solvent-soluble quinolone salt with a dimethylformaide dialkyl acetal in an organic solvent such as chloroform, dimethylformamide or methanol. The alkyl group of the acetal function may be lower alkyl or branched alkyl as described previously. The preferred alkyl group is methyl and, thus, the preferred reagent for this transformation is dimethylformamide dimethyl acetal. For example, treatment of the tetra-n-butyl ammonium salt of compound V with dimethylformamide dimethyl acetal in refluxing methanol for 10 to 60 hours, yields the compounds of formula XI.

XI→X→IB

Reaction of the compound of formula XI with a beta-lactam of the formula

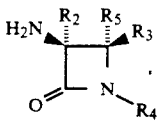

in the presence of a base such as triethylamine or diisopropylamine, in an organic solvent such as dichloromethane, chloroform, acetonitrile or dimethylformamide, at ambient temperature for about 2 to 10 hours, yields the amidino compound of formula X. The base is required to neutralize any acidic functionality in $R_3$ and/or $R_4$. Alternatively, if any acidic functions contained in $R_3$ and/or $R_4$ have been selectively blocked with a readily removable protecting group, such as by standard methods known in the art, then the base may be omitted. For example, reaction of the compound of formula XI in which $R_c$ is —CH(OCH$_3$)$_2$, with desacetoxy-7-cephalosporanic acid in anhydrous dimethylformamide for about 4 to 10 hours, gives compound X in which $R_2$ and $R_5$ are hydrogen and $R_3$ and $R_4$ together form the dihydrothiazine ring of a cephalosporin, that is,

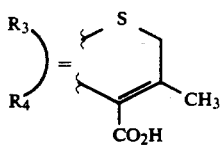

The final product in the sequence may be isolated as a salt or as the free acid, by methods standard to the art. Thus, in the above example addition of a solution of sodium-2-ethylhexanoate in the ethyl acetate results in the precipitation of the corresponding disodium salt of compound IB.

SCHEME 3

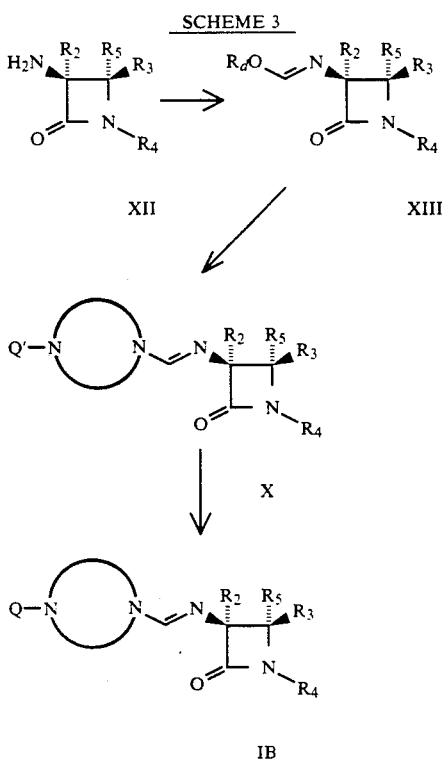

Q' = ester or soluble salt of Q.
$R_d$ = lower alkyl.

Scheme 3

XII→XIII

A compound of formula XII, preferably with the acidic group in $R_4$ being selectively blocked with a readily removable protecting group, as by methods standard to one skilled in the art, is first converted to the corresponding imidic ester β-lactam, the compound XIII. This may be accomplished in one of two ways. The first involves the reaction of the suitably protected β-lactam of formula XII with an α,α-dichloromethyl-alkyl ether, preferably α,α-dichloromethyl-methyl ether, in an inert solvent such as chloroform for 10–24 hours at room temperature, in the presence of a tertiary amine such as triethylamine. The second, and more preferred, method involves the reaction of compound XII with a formimidic ester hydrochloride (prepared as described in *Angew. Chem.*, 1967, 79, 531), of the formula

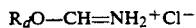

Thus, treatment of the suitable protected β-lactam XII (as described previously) with the formimidic ester hydrochloride in a suitable inert solvent, for 1–5 hours at room temperature, gives the desired N-alkoxy-methylene-β-lactam a compound of formula XIII in good yield. The formimidic ester hydrochloride should be either the methyl or more preferably, the isopropyl formimidic ester hydrochloride, i.e., $R_d$ is $CH_3$ or $-CH(CH_3)_2$. The preferred solvents for this reaction are tetrahydrofuran or dichloromethane.

XIII→X

Compound XIII is then converted without isolation into the amidino β-lactam compound of formula X, by reaction with a suitably protected quinolone containing a secondary nitrogen atom as previously described. The reaction is preferably carried out in the same solvent used to form the N-alkoxy-methylene derivative of formula XIII, at room temperature for 1–10 hours. The protecting group on the quinolone is chosen such that its subsequent removal is compatible with the β-lactam function and the newly formed amidino group. The preferred protecting group for the carboxylic acid group in the quinolone is the p-nitrobenzyl ester group. Alternatively, the quinolone carboxylic acid group may be converted into a soluble tetra-alkyl ammonium salt, preferably, the tetra-n-butyl ammonium salt, for the subsequent reaction of compound VIII with compound XIII.

X→IB

The protected carboxylic acid group in the compound of formula X is converted into the free carboxylic acid group, using conventional methods such that the rest of the molecule is unaffected. Additionally, the acid-protecting group in $R_4$ is removed by methods compatible with the preceding restrictions. For instance, in the case of compound X containing the preferred p-nitrobenzyl ester function as the protecting group on both the quinolone and $R_4$ carboxylic acid groups, and where $R_2$ and $R_5$ are hydrogen and $R_3$ and $R_4$ together form the thiazolidine ring of a penam, i.e. 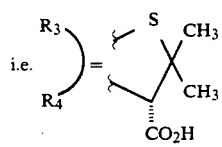

deprotection of both carboxylic acid groups may be carried out simultaneously by a catalytic hydrogenation process. This is preferably conducted at atmospheric pressure with a supported catalyst such as palladium-on-carbon, in an appropriate solvent such as aqueous tetrahydrofuran, to give the compound of formula IB.

SCHEME 4

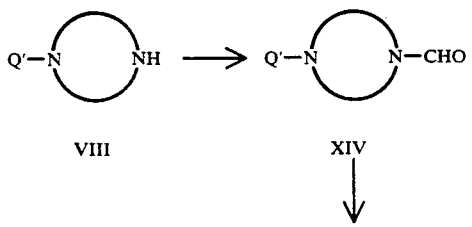

VIII        XIV

SCHEME 4

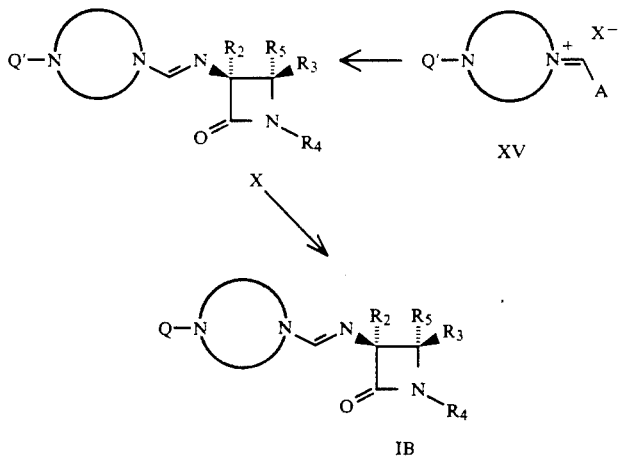

A = Cl, OR$_d$, SR$_d$
X = Cl$^-$, BF$_4^-$, MeSO$_4^-$
R$_d$ = lower alkyl.
Q' = ester derivative of Q

Scheme 4

VIII→XIV

A compound of formula VIII, selectively protected on the carboxylic acid function as an ester derivative, Q', is formylated on the secondary nitrogen atom by reaction with formyl acetyl anhydride, in an inert solvent such as dichloromethane, to give the compound of formula XIV. The ester group can be, for example, tert-butyl, p-nitrobenzyl, benzhydryl, allyl, 2,2,2-trichloroethyl or 2-trimethylsilylethyl. The preferred choice of ester functions is one which can be readily removed after amidino formation without affecting either the β-lactam ring or the amidino function. A preferred carboxylic acid protecting group is the p-nitrobenzyl group.

XIV→XV

For activation via the imminium chloride route (A=Cl, X=Cl$^-$), a compound of formula XIV is treated with phosgene or oxalyl chloride in a suitably inert solvent such as ether, tetrahydrofuran, dichloromethane or, preferably, chloroform, at from −20° C. to room temperature for 1-24 hours, to give the imminium chloride, compound XV (A═Cl, X═Cl$^-$).

XV→X

The compound of formula XV is then reacted with the free amino group of a β-lactam of the formula

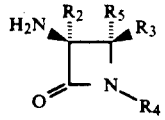

in an inert solvent such as chloroform, in the presence of a tertiary amine such as triethylamine, to give the amidino-β-lactam of formula X. Any acidic function in R$_4$ is selectively protected, preferably as an ester function such as p-nitrobenzyl or trialkylsilyl. Thus, for example, reaction of a protected N-formyl quinolone of formula VIII with oxalyl chloride in dichloromethane at −20° C. for one hour, gives the corresponding imminium chloride, of formula XV (A═X═Cl). This is then reacted with the trimethylsilyl ester for 6-APA in the presence of triethylamine at −20° C. for one hour to give a compound of formula X in which R$_2$ and R$_5$ are hydrogen and R$_3$ and R$_4$ together form the thiazolidene ring of a penam.

An alternative to activation via the imminium chloride involves the use of imminium ethers or thioethers for activation of the tertiary acid amide groups. Thus, for instance, treatment of a protected N-formyl quinolone of formula XIV with Meerweins reagent (Et$_3$O$^+$BF$_4^-$) gives the corresponding imminium methyl ether of formula XV (A═OCH$_3$, X═CH$_3$SO$_4$). If the corresponding thioamide is used instead of the N-formyl analog, compound XIV, then the imminium thioether may be obtained. Either of these compounds can then be converted to the amidino-β-lactam compound of formula X, as previously described for the imminium chloride activation method.

X→IB

Compound X is then converted to compound IB in the same way as described in Scheme 3.

The invention is further illustrated in the Examples which follow.

EXAMPLE 1

1-Ethyl-6-fluoro-1,4-dihydro-7-[4-[1,1-dimethylethoxy)carbonyl]-1-piperazinyl]-4-oxo-3-quinolone carboxylic acid

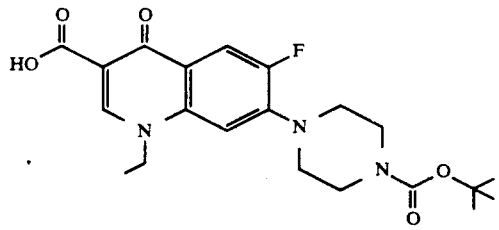

To a stirred suspension of norfloxacin (24.0 g, 0.075 mol) in dioxane (240 mL) was added water (130 mL) and 1N aqueous sodium hydroxide (79.9 mL, 0.080 mol) and the resulting mixture was heated at 100° C. until a clear solution was obtained (approximately 30 minutes).

The solution was then cooled to 0° C., and a solution of di-tert-butyl dicarbonate (19.2 g, 0.088 mol) in dioxane (50 mL) was added. The temperature was maintained at 0° C. for 30 minutes, then allowed to rise to ambient temperature, and the mixture was then stirred for a further 3 hours. The mixture was filtered and the precipitate was suspended in 10% aqueous acetic acid (520 mL), heated at 100° C. for a few minutes, allowed to cool and filtered. The product was dried to give t-BOC-norfloxacin (5, 27.0 g, 86% yield) as a white solid.

EXAMPLE 2

1-Ethyl-6-fluoro-1,4-dihydro-7-[4-[(1,1-dimethylethoxy)carbonyl]-1-piperazinyl]-4-oxo-3-quinolinecarboxylic acid methyl ester

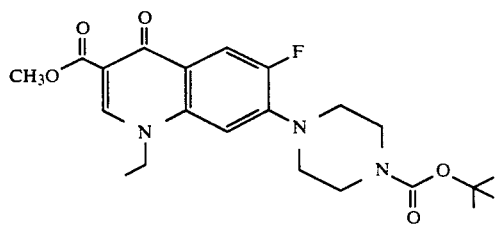

To a suspension of t-BOC-norfloxacin (1.0 g, 2.4 mmol) in methanol (50 mL) was added excess diazomethane and the mixture stirred at ambient temperature for 2½ hours. Removal of solvent provided the desired product (1.03 g, 100% yield).

EXAMPLE 3

1-Ethyl-6-fluoro-1,4-dihydro-4-oxo-7(1-piperazinyl)-3-quinolinecarboxylic acid methyl ester

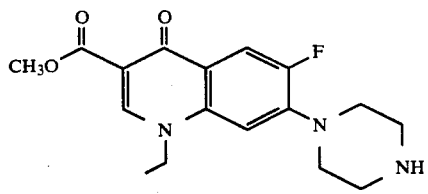

A mixture of t-BOC-norfloxacin methyl ester (1.2 g, 2.77 mmol), anisole (10 mL) and trifluoroacetic acid (10 mL) was stirred at 0° C. for 3 hours. The mixture was evaporated at ambient temperature under high vacuum to provide a residue, which was then suspended in water (50 mL) and the pH was adjusted to 10-11 with 1N sodium hydroxide. The mixture was extracted with dichloromethane (3×75 mL). The combined organic extracts were dried (Na₂SO₄), and solvent was removed to give the product, norfloxacin methyl ester (0.68 g, 86% yield) as a white solid; melting point: 189°-190° C.

EXAMPLE 4

1-Ethyl-1,4-dihydro-6-fluoro-7-[4-dimethoxymethyl)-1-piperazinyl]-4-oxo-3-quinolinecarboxylic acid methyl ester

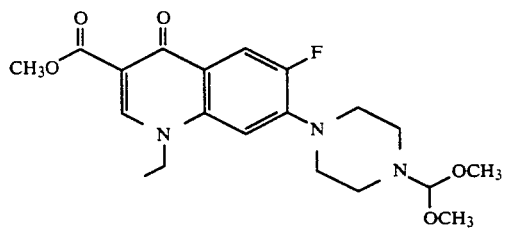

Norfloxacin methyl ester (0.5 g, 0.0015 mol) was refluxed in dimethylformamide dimethylacetal (15.0 mL) for 6 hours. Removal of the excess DMF-acetal under high vacuum gave the desired acetal.

EXAMPLE 5

[2S-(2α,5α,6β)]-6-[[[4-[1-Ethyl-6-fluoro-1,4-dihydro-3-(methoxycarbonyl)-4-oxo-7-quinolinyl]-1-piperazinyl]-methylene]amino]-3,3-dimethyl-6-oxo-4-thia-1-azabicyclo[3.2.0]heptane-2-carboxylic acid

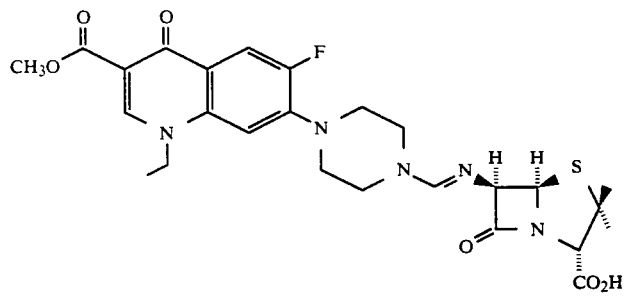

To a suspension of 6-aminopenicillanic acid (0.308 g, 14.2 mmol) in chloroform (10 mL) was added diisopropylethylamine (0.247 mL, 0.183 g, 14.2 mmol) and the mixture stirred at ambient temperature for 30 minutes. The solution was cooled at 0° C. and a solution of the acetal from Example 4 (15 mmol) in anhydrous chloroform (10 mL) was added. The mixture was stirred at 0° C. for 1 hour, then at ambient temperature for 4 hours. The solvent was removed at room temperature, water (50 mL) was added and the pH was adjusted to 6 with 1N hydrochloric acid. The resulting solution was freeze-dried, and the crude product was purified by preparative liquid chromatography (C-18 reverse phase, gradient 0-100% methanol in water) to give, after lyophilization, the product as a white powder.

EXAMPLE 6

1-Ethyl-6-fluoro-1,4-dihydro-7-[4-[(1,1-dimethylethoxy)carbonyl]-1-piperazinyl]-4-oxo-3-quinolinecarboxylic acid (4-nitrophenyl)methyl ester

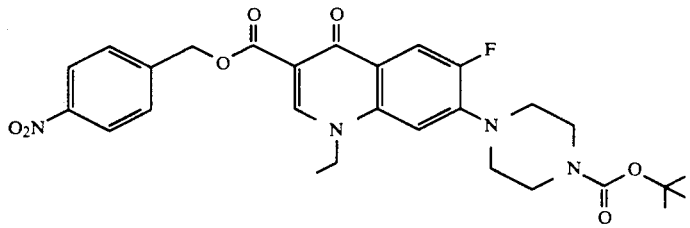

To a stirred suspension of t-BOC-norfloxacin (1.0 g, 2.4 mmol) in water (40 mL) was added 1N sodium hydroxide (2.5 mL, 2.5 mmol) and the mixture was warmed until a clear solution was obtained. The solution was filtered and freeze-dried to gives the sodium salt, which was then dissolved in dimethylformamide (10 mL). Molecular sieves (Type 4A°) were added and the mixture was stirred for 2 hours, after which p-nitrobenzyl bromide (0.55 g, 2.5 mmol) was added and the reaction was then stirred at ambient temperature for 3 days. The sieves were removed by filtration and solvent was then removed under reduced pressure. The residue was purified by flash chromatography (silica gel, dichloromethane:ethyl-acetate-1:2 as eluant) to give the product (1.0 g, 77% yield), as a white solid.

EXAMPLE 7

1-Ethyl-6-fluoro-1,4-dihydro-4-oxo-7(1-piperazinyl)-3-quinolinecarboxylic acid (4-nitrophenyl)methyl ester

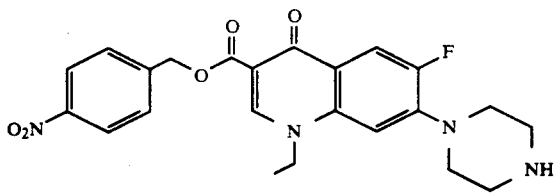

A mixture of t-BOC-norfloxacin-p-nitrobenzyl ester (10 g 0.018 mol), anisole (40 mL) and trifluoroacetic acid (40 mL) was stirred at 0° C. for 3 hours. The mixture was evaporated at room temperature under high vacuum and the residue triturated with diethyl ether (2×100 mL). The ether extract was washed with water (2×100 mL) and the residue from the trituration and the water washings were combined, the pH was adjusted to 11 (using 1N NaOH), and the aqueous solution was extracted with dichloromethane (7×100 mL). The combined organic extracts were dried (Na₂SO₄) and the solvent was removed to give the product norfloxacin p-nitrobenzyl ester (7.7 g, 95% yield) as a white solid.

EXAMPLE 8

1-[Bix(2,2-dimethylpropoxy)methyl]-4-phenylpiperazine

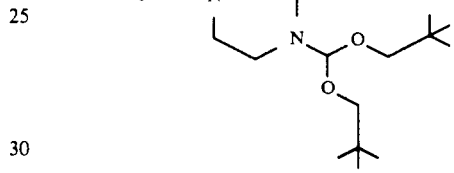

A solution of 4-phenylpiperazine (0.162 g, 0.001 mol) and dimethylformamide dineopentyl acetail (0.346 g, 0.0015 mol) in anhydrous chloroform (5 mL) was refluxed for 10 hours. The solvent and excess reagent were removed (100° C./1 mm) to give the product in quantitative yield.

EXAMPLE 9

[2s-(2α,5α,6β)]-3,3-Dimethyl-7-oxo-6]][(4-phenyl-1-piperazinyl)methylene]-amino]-4-thia-1-azabicyclo[3.2.0]heptane-2-carboxylic acid

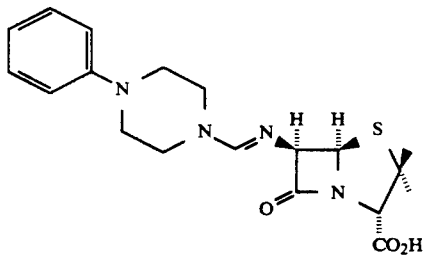

A mixture of 6-aminopenicillanic acid (0.216 g, 0.001 mol) and diisopropylethylamine (0.129 g, 0.174 mL, 0.001 mol) in anhydrous chloroform (6 mL) was stirred at ambient temperature for 30 minutes, and then was cooled to 0° C. To this solution was added the phenylpiperazine acetal product from Example 8 (0.001 mol), in anhydrous chloroform (5 mL), and the mixture was stirred at room temperature for 2 hours. The solvent was removed, water was added and the pH was adjusted to 5 (1N HCl). The aqueous solution was applied to a flash column (C-18 reverse phase, gradient 0-100% acetonitrile in water), to give, after lyophilization of the appropriate fractions, the product as a white powder.

EXAMPLE 10

1-Ethyl-6-fluoro-1,4-dihydro-7-[4-[bis(2,2-dimethylpropoxy)methyl]-1-piperazinyl]-4-oxo-3-quinoline carboxylic acid (4-nitrophenyl)methyl ester

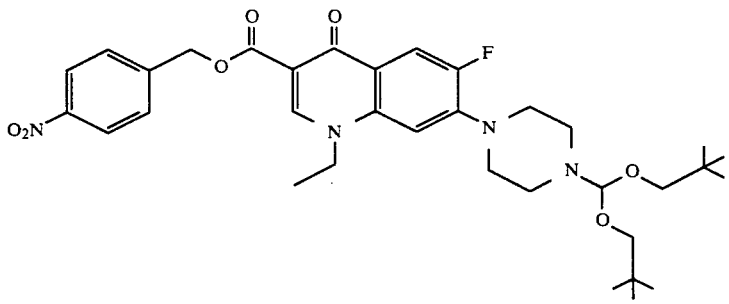

A solution of norfloxacin-p-nitrobenzyl ester (2.6 g, 4.76 mmol) and dimethylformamide-dineopentyl acetal (6.6 g 28.4 mmol) in anhydrous chloroform (75 mL) was heated at reflux for 12 hours. The solvent and excess reagent were removed (90° C./1 mm) to give the desired product as a white solid.

EXAMPLE 11

[2s-(2α,5α6β)]-7-[4-[[[2-(Carboxy)-3,3-dimethyl-7-oxo-4-thia-1-azabicyclo-[3.2.0]hept-6-yl]imino]methyl]-1-piperazinyl
]1-ethyl-6-fluoro-1,4-dihydro-4-oxo-3-quinolinecarboxylic acid (4-nitrophenyl)methyl ester monosodium salt

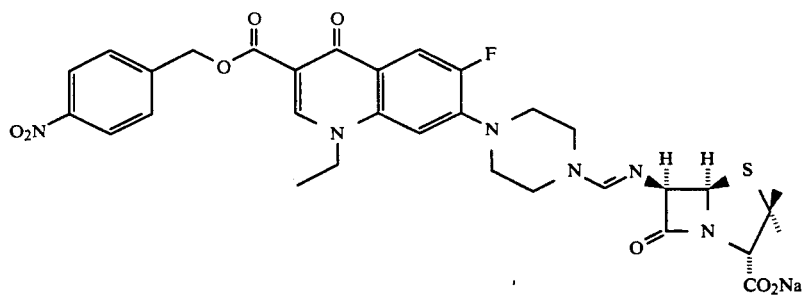

A solution of the diisopropylethylammonium salt of 6-aminopenicillanic acid in anhydrous chloroform (60 mL) was prepared from 6-aminopenicillanic acid (0.97 g, 4.5 mmol) and diisopropylethylamine (0.77 mL, 0.57 g, 4.5 mmol). To this solution at ambient temperature was added the quinolone dineopentylacetal product from Example 10 (4.76 mmol), in anhydrous chloroform (60 mL), and the resulting mixture was stirred for 4½ hours. A solution of sodium-2-ethylhexanoate (1.8 g, 10.8 mmol) in ethyl acetate (20 mL) was added and solvent was removed under reduced pressure. The residue was dissolved in water and purified by preparative liquid chromatography (C-18 reverse phase, gradient 0–100% acetonitrile in water) to give after lyophilization the protected quinolone amidino penicillin as a white powder (1.1 g, 35% yield).

EXAMPLE 12

[2S-(2α,5α,6β)]-7-[4-[[[2-(Carboxy)-3,3-dimethyl-7-oxo-4-thia-1-azabicyclo[3.2.0]hept-6-yl]imino]methyl]-1-piperazinyl]-1-ethyl-6-fluoro-1,4-dihydro-4-oxo-3-quinolinecarboxylic acid monosodium salt

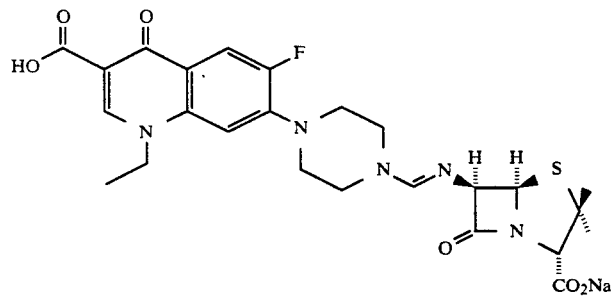

The p-nitrobenzylester product from Example 11 (1.0 g, 2.42 mmol) in tetrahydrofuran:water (1:1, 100 mL) was hydrogenated over 10% palladium on carbon (1.0 g) at atmospheric pressure and ambient temperature for 2 hours. The catalyst was removed by filtration and the tetrahydrofuran was removed under reduced pressure. The aqueous layer was washed with ethyl acetate (2≈25 mL) and purified by preparative liquid chromatography (C-18 reverse phase, gradient 0–80% acetonitrile in water). After removal of the acetonitrile from the combined appropriate fractions, the aqueous solution was freeze-dried to give the desired product as a white solid.

EXAMPLE 13

(6R-trans)-7-[4-[[[3-[(Acetyloxy)methyl]-2-carboxy-8-oxo-5-thia-1-azabicyclo[4.2.0]oct-2-en-7-yl]imino]methyl]-1-piperazinyl]-1-ethyl-6-fluoro-1,4-dihydro-4-oxo-3-quinoline carboxylic acid (4-nitrophenyl)methyl ester monosodium salt

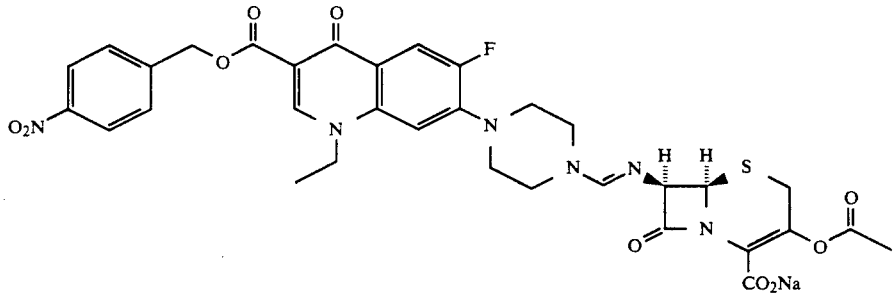

A solution of norfloxacin p-nitrobenzylester dineopentyl acetal (0.26 mmol, prepared from norfloxacin p-nitrobenzyl ester, 120 mg, 0.26 mmol) in anhydrous chloroform, 3 mL, was added to a solution of 7-aminocephalosporanic acid (70 mg, 0.26 mmol) in anhydrous chloroform (4 mL). Diisopropylethylamine (40 mg, 0.31 mmol) was added and the mixture stirred at ambient temperature for 4 hours. A solution of sodium-2-ethylhexanoate (100 mg, 0.6 mmol), in ethyl acetate (1 mL) was added and the mixture was stirred for 45 minutes. The crude sodium salt was filtered off and purified by C-18 flash chromatography (step gradient, 0-100% acetonitrile in water). Acetonitrile was removed under reduced pressure from the combined fractions and the remaining aqueous solution was lyophilized to give the product as a pale yellow powder (44.5 mg, 24% yield).

EXAMPLE 14

(6R-trans)-7-[4-[[[3-[(Acetyloxy)methyl]-2-carboxy-8-oxo-5-thia-1-azabicyclo[4.2.0]oct-2-en-7-yl]imino]methyl]-1-piperazinyl]-1-ethyl-6-fluoro-1,4-dihydro-4-oxo-3-quinoline carboxylic acid monosodium salt

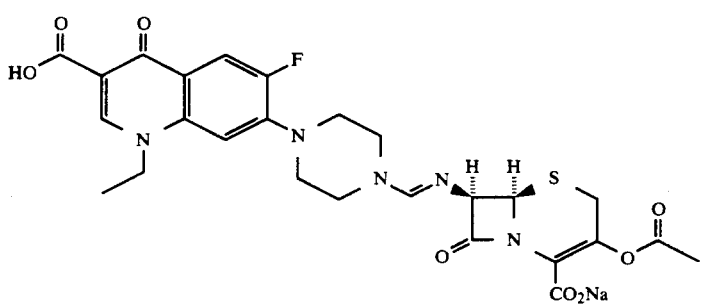

The p-nitrobenzyl protected quinolone cephalosporin from Example 13 (40 mg, 0.053 mmol) in tetrahydrofuran:water (1:1,8 mL) was hydrogenated over 10% palladium on carbon (38 mg) at 1 atmosphere and ambient temperature for 1½ hours. Workup as in the previous Example provided the product as a white lyophilized powder (10 mg, 31% yield).

EXAMPLE 15

1-Ethyl-1,4-dihydro-6-fluoro-7-[4-(dimethoxymethyl)-1-piperazinyl]-4-oxo-3-quinolinecarboxylic acid (1:1) N,N,N-tributyl-1-butylammonium salt

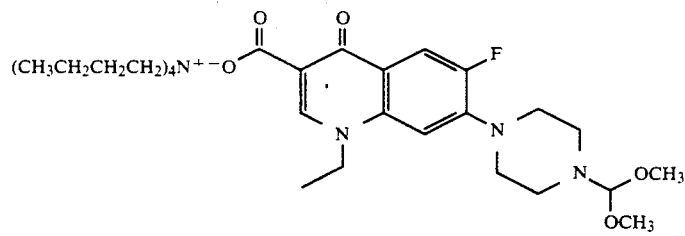

A solution of sodium hydroxide (6.2 mL, 1N, 6.2 mmol) was added to a mixture of norfloxacin (1.0 g, 3.1 mmol) and tetrabutylammonium bisulfate (1.06 g, 3.1 mmol) in water (20 mL). The mixture was stirred until a clear solution was obtained and then was lyophilized. The resulting solid was triturated with anhydrous dichloromethane (3×20 mL) and the insolubles were removed by filtration. The filtrate was evaporated to dryness under reduced pressure to give the tetra-n-butylammonium salt of the quinolone. The soluble quinolone salt was dissolved in anhydrous methanol (25 mL) and dimethylformamide-dimethyl acetal (5 mL), and then it was heated at reflux for 16 hours. The solvent was removed under reduced pressure (10 mm Hg) and the excess acetal was removed at 50° C. (0.5 mm Hg), to give the product, which was the tetra-n-butylammonium salt of norfloxacin dimethyl acetal. This material was used directly in the coupling reaction.

An alternative to the above procedure involves omitting the dichloromethane trituration step to isolate the quinolone salt. Instead the lyophilized material is suspended in methanol and dimethylformamide dimethyl acetal and heated at reflux for 16 hours, then allowed to cool, filtered and evaporated to give the desired product.

EXAMPLE 16

[2s-(2α,5α,6β)]-7-[4[[[2-(Carboxy)-3,3-dimethyl-7-oxo-4-thia-1-azabicyclo[3.2.0]hept-6-yl]imino]methyl]-1-piperazinyl]-1-ethyl-6-fluoro-1,4-dihydro-4-oxo-4-quinolinecarboxylic acid disodium salt

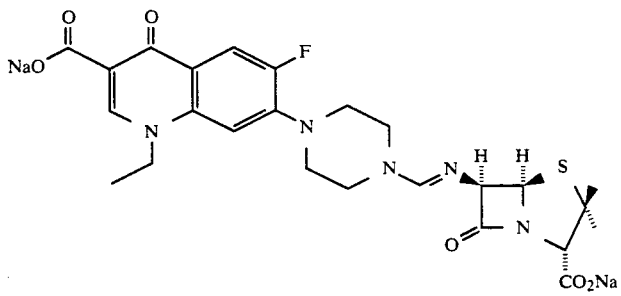

To a solution of the tetra-n-butylammonium salt of norfloxacin dimethylacetal, made as described in Example 15 from norfloxacin (1.6 g, 5.0 mmole) in anhydrous chloroform (40 mL), was added 6-aminopenicillanic acid (0.973 g, 4.5 m,mol) and diisopropylethylamine (0.58 g, 0.78 μL, 4.5 mmol). The resulting solution was stirred at room temperature for 4 hours and a solution of sodium-2-ethylhexanoate (1.83 g, 11 mmol) in ethylacetate (30 mL) was then slowly added. The crude product was isolated by filtration (2.9 g; hygroscopic) and purified by preparative liquid chromatography (C-18 reverse phase, gradient, 0–100% acetonitrile in water). The appropriate fractions were combined and lyophilized to give the desired product (1.06 g, 39% yield) as the disodium salt.

EXAMPLE 17

[6R-[6α,7β(E)]]-7-[4-[[(2-Carboxy-3-methyl-8-oxo-5-thia-1-aza-bicyclo[4.2.0]oct-2-en-7-yl)imino]-methylπ-1-piperazinyl]-1-ethyl-6-fluoro-1,4-dihydro-4-oxo-3-quinolinecarboxylic acid disodium salt

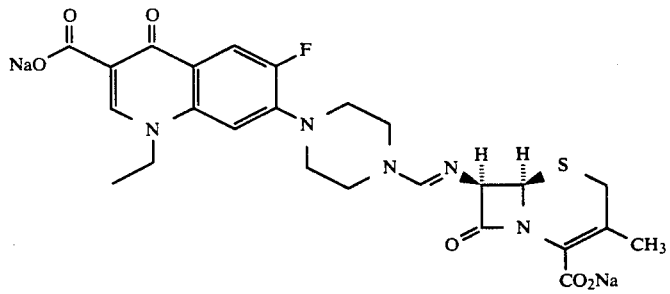

To a solution of the tetra-n-butylammonium salt of norfloxacin dimethylacetal, made from norfloxacin (0.32 g, 1 mmol) as described, in anhydrous dimethylformamide (10 mL) was added desacetoxy-7-aminocephalosporanic acid (0.21 g, 1 mmol) and diisopropylethylamine (0.13 g, 0.174 mL, 1 mmol). The resulting solution was stirred at ambient temperature for 4 hours and a solution of sodium-2-ethyl-hexanoate (0.36 g, 2.2 mmol) in ethyl acetate (6 mL) was added. The resulting precipitate was filtered, washed with ethyl acetate and dried (0.5 g). The crude product was purified by preparative liquid chromatography (C-18 reverse phase, gradient, 0–50% acetonitrile in water). Lyophilization of the appropriate fractions provided the desired disodium salt as a white powder (0.155 g, 26% yield).

EXAMPLE 18

1-Ethyl-6-fluoro-1,4-dihydro-7-[4-[(1-formyl-4-piperidinyl)methyl]-1-piperazinyl]-4-oxo-3-quinolinecarboxylic acid

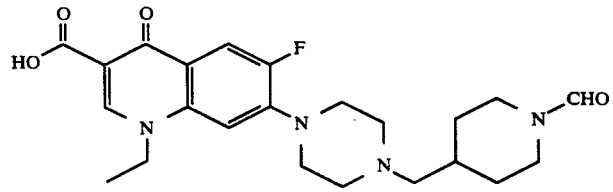

A mixture of norfloxacin (0.96 g, 3 mmol), 4-bromomethyl-1-formylpiperidine (1.26 g, 6.1 mmol) and triethylamine (0.44 g, 0.6 mL, 4.3 mmol) in anhydrous dimethylformamide (15 mL) was heated at 100° C. for 2 hours. The solvent was removed under high vacuum and the residue was dissolved in methanol, filtered and precipitated by the addition of diethyl ether to give the product as a white solid (1.0 g, 75% yield).

EXAMPLE 19

1-Ethyl-6-fluoro-1,4-dihydro-4-oxo-7-[4-(4-piperidinylmethyl)-1-piperazinyl]-3-quinolinecarboxylic acid was collected, washed with water and dried to give the desired product.

EXAMPLE 21

1-Ethyl-6-fluoro-1,4-dihydro-7-[4-[[1-[(dimethoxy)methyl]-4-piperidinyl]methyl]-1-piperazinyl]-4-oxo-3-quinolinecarboxylic acid N,N,N,-tributyl-1-butylammonium (1:1) salt

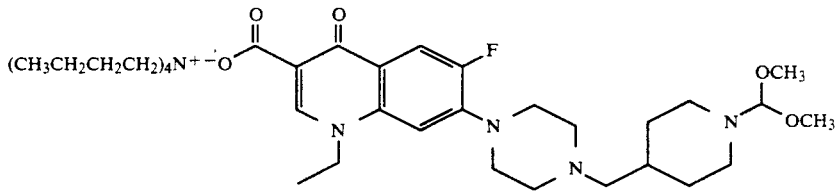

monohydrochloride

A mixture of the compound prepared in Example 20

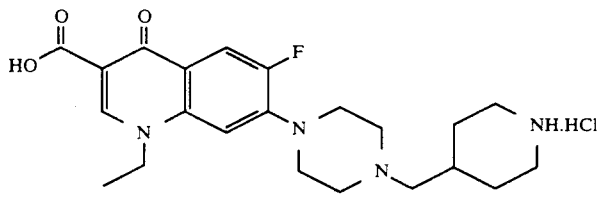

A solution of the N-formylquinolone from Example 18, (1.0 g, 2.25 mmol) in dioxane (20 mL) and aqueous hydrochloric acid (1N, 20 mL) was heated at 100° C. for 3½ hours. The solvent was removed and the residue was recrystallized from methanal to give the product as a white crystalline solid (0.85 g, 85% yield).

EXAMPLE 20

1-Ethyl-6-fluoro-1,4-dihydro-4-oxo-7-[4-[(4-piperidinyl)methyl]-1-piperazinyl]-3-quinolinecarboxylic acid (0.416 g, 1 mmol), tetra-n-butylammonium hydrogen sulfate (0.339 g, 1 mmol) and aqueous sodium hydroxide (1N, 2.0 mL, 2 mmol) in water (5.0 mL) was stirred until a clear solution was obtained and then was freeze-dried to give the tetra-n-butyl ammonium salt of the quinoline. To the lyophilized solid was added methanol (10 mL) and dimethylformamide dimethyl acetal (10 mL), and the mixture was then heated at reflux overnight (20 hours). After filtration, the solvent was removed to give the tetra-n-butylammonium salt of the quinolone dimethyl acetal.

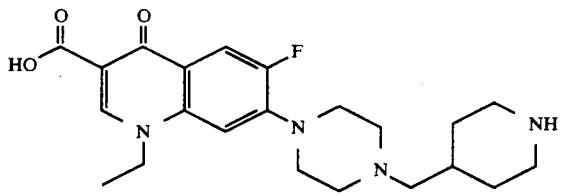

The free base was prepared from the hydrochloride (from Example 19) by dissolving the hydrochloride in water (15 mL/2 g of hydrochloride) and adding saturated aqueous sodium bicarbonate until the pH exceeded 8. After stirring for 15 minutes, the precipitate

EXAMPLE 22

[2s-(2α,5α,6β)]-7-[4-[[1-[[(2-Carboxyl-3,3-dimethyl-7-oxo-4-thia-1-azabicyclo[3.2.0]hept-6-yl)imino]methyl]-4-piperidinyl]methyl]-1-piperazinyl]-1-ethyl-6-fluoro-1,4-dihydro-4-oxo-3-quinolinecarboxylic acid monosodium salt

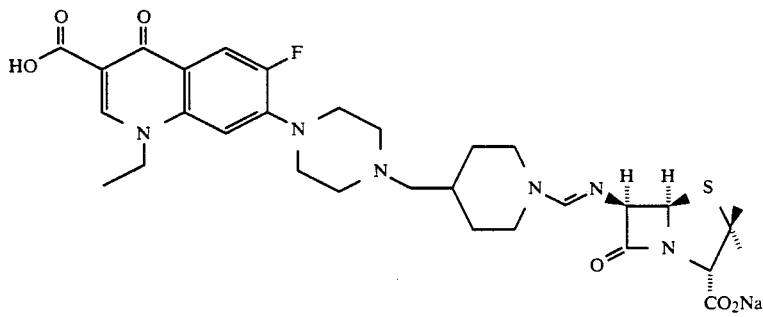

To a solution of the tetra-n-butylammonium salt of the quinolone dimethyl acetal prepared in Example 21 (1 mmol), in anhydrous chloroform, was added 6-aminopenicillanic acid (0.216 g, 1 mmol) and diisopropylethylamine (0.13 g, 0.174 mL, 1 mmol). The mixture was stirred at ambient temperature for 5 hours and a solution of sodium-2-ethylhexanoate (0.339 g, 2 mmol) in ethyl acetate (10 mL) was added. The precipitate was filtered off and dried to give the crude product (800 mg) as the sodium salt. The crude product was purified by preparative liquid chromatography (C-18 reverse phase, 0–100% aqueous acetonitrile gradient) to provide, after lyophilization, the desired quinolone amidino-β-lactam product as a white powder (0.17 g, 26% yield).

EXAMPLE 23 rac-1-Ethyl-6-fluoro-1,4-dihydro-7-(3-methyl-1-piperazinyl)-4-oxo-3-quinoline-carboxylic acid monosodium salt

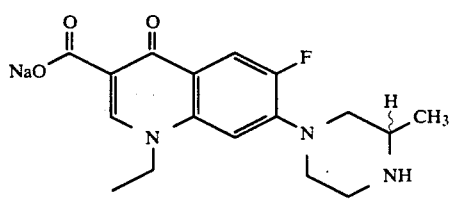

A mixture of 7-chloro-1-ethyl-6-fluoro-1,4-dihydro-4-oxo-3-quinolinecarboxylic acid [*J. Med. Chem.*, 23, 1358 (1980)] (0.52 g, 2 mmol) and 2-methylpiperazine (0.8 g, 8 mmol) was heated at 175° for 5 hours. The residue was dissolved in ethylacetate (10 mL) and chloroform (10 mL), and a solution of sodium-2-ethyl-hexanoate (0.33 g, 2 mmol) in ethyl acetate (20 mL) was added. The mixture was stirred for 30 minutes and the precipitate was collected. The crude product was purified by preparative liquid chromatography (C-18 reverse phase, gradient 0–40% acetonitrile in water) to give a pale yellow lyophilized solid (0.5 g, 75% yield).

EXAMPLE 24

Rac-1-Ethyl-6-fluoro-1,4-dihydro-7-(3-methyl-1-piperazinyl)-4-oxo-3-quinoline-carboxylic acid-N,N,N,-tributyl-1-butylammonium (1:1) salt

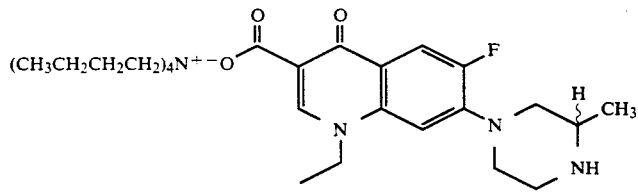

This was prepared from the sodium salt prepared in Example 23 (0.5 g, 1.5 mmol) in water (2 mL) by addition of aqueous sodium hydroxide (1.5 mmol, 1.5 mL of 1N) and tetrabutyl ammonium hydrogen sulfate (0.68 g, 2mmol) dissolved in water (4mL), followed by extraction with dichloromethane (4×10 mL). The organic extract was dried (using Na$_2$SO$_4$) and the solvent was removed to give the product.

EXAMPLE 25

[2s-(2α,5α,6β)]-7-[4-[[(2-Carboxy-3,3-dimethyl-7-oxo-4-thia-1-azabicyclo-[3.2.0]hept-6-yl)amino]methylene]-3-methyl-1-piperazinyl]-1-ethyl-6-fluoro-1,4-dihydro-4-oxo-3-quinoline carboxylic acid monosodium salt

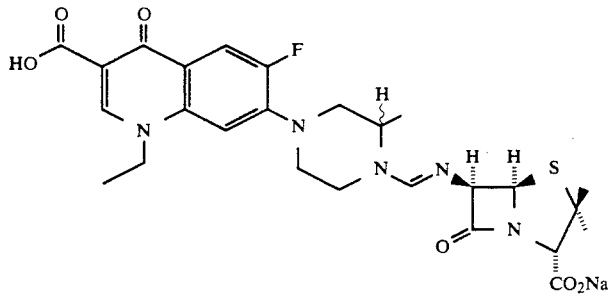

To a solution of the tetrabutylammonium salt prepared in Example 24 (1.5 mmol) in anhydrous methanol (5.0 mL) was added dimethylformamide dimethyl acetal (5.0 mL). The mixture was heated at reflux for 60 hours. Solvent and excess reagent were removed under high vacuum to give the crude quinolone dimethyl acetal, which was dissolved in chloroform (5.0 mL) and added to a solution of 6-aminopenicillanic acid (0.43 g, 2 mmol) and diisopropylethylamine (0.26 g, 0.348 mL, 2 mmol) in chloroform (20 mL). The resulting solution was stirred at ambient temperature for 4½ hours and then a solution of sodium-2-ethyl-hexanoate (0.68 g, 4 mmol) in ethyl acetate (20 mL) was added. The resulting precipitate was filtered and purified by preparative liquid chromatography (C-18 reverse phase, 0-100% aqueous acetonitrile gradient) to give the product as a white lyophilized powder.

EXAMPLE 26

6,8-Difluoro-1-(2-fluoroethyl)-1,4-dihydro-7-(4-methyl-1-piperazinyl)-3-quinolinecarboxylic acid ethyl ester

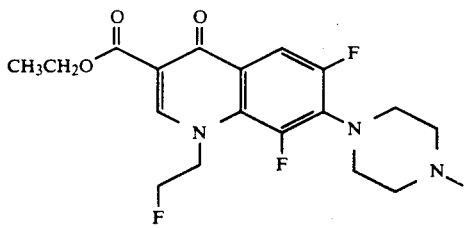

To a stirred suspension of 6,8-difluoro-1-(2-fluoroethyl)-1,4-dihydro-7-(4-methyl-1-piperazinyl)-4-oxo-3-quinolinecarboxylic acid (Fleroxacin; Belgian Patent No. 887,574) (35 g, 0.095 mol) in anhydrous ethanol (2.0 L) was added dropwise thionyl chloride (184 mL, 2.52 mol) over a 2-hour period. The solution was then heated at reflux and monitored by thin layer chromatography, until all starting material had been consumed (at this point a clear solution was obtained). The mixture was evaporated to dryness (36.3 g) and recrystallized from ethanol to give a white crystalline solid (30.4 g, 81% yield).

EXAMPLE 27

7-[4-[(Ethenyloxy)carbonyl]-1-piperazinyl]-6,8-difluoro-1-(2-fluoroethyl)-1,4-dihydro-4-oxo-3-quinolinecarboxylic acid ethyl ester

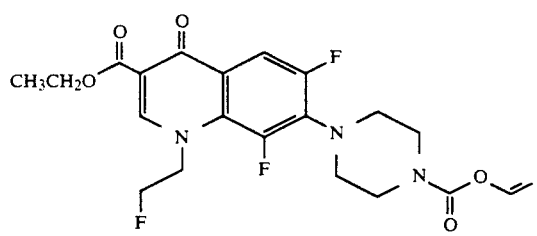

To a stirred, cooled (−65° C.) solution of vinylchloroformate (7.8 mL, 0.085 mol) in anhydrous dichloromethane (650 mL) was added dropwise a solution of the ethyl ester product from Example 26 (26.0 g, 0.066 mol), in anhydrous dichloromethane (500 mL). The rate of addition was such that the total time involved was 1 hour and the mixture was allowed to slowly come to ambient temperature (at 3° C., a gas was evolved). The mixture was then stirred at reflux for 6 hours and solvent was removed to give the crude product (29.6 g). The crude product was purified by preparative liquid chromatography (silica, 5% ethanol in chloroform as eluant) to give the desired vinyl carbamate product as a white powder (27.1 g, 71% yield): mp 151°–151.5° C. (from ethanol).

EXAMPLE 28

6,8-Difluoro-1-(2-fluoroethyl)-1,4-dihydro-4-oxo-7-(1-piperazinyl)-3-quinolinecarboxylic acid

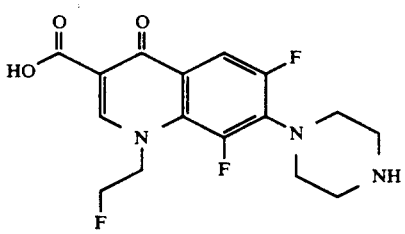

A stirred solution of the vinyl carbamate from Example 27 (5.0 g, 0.011 mol) in anhydrous dichloromethane (300 mL) was saturated with dry hydrogen chloride gas. The mixture was stirred for 2 hours at ambient temperature while gaseous hydrogen chloride was bubbled into the solution, during which time a deep amber color developed. The mixture was concentrated to dryness, giving a gummy solid, which was suspended with stirring in 1N aqueous hydrochloric acid. The mixture was heated at reflux for 2½ hours, during which all of the material went into solution. The solution was cooled and stored overnight in a refrigerator. The precipitate was collected by filtration and dried (3.9 g). This solid was dissolved in hot water (200 mL) and filtered, the pH was adjusted to 7 with solid sodium bicarbonate, and the resulting mixture was allowed to stand at room temperature for 3 hours. The crystalline precipitate was collected, washed with cold water and dried to give the product as a white crystalline solid (3.4 g, 87% yield): mp 271°–273° C. (decomp).

was stirred at ambient temperature for 6 hours, and then a solution of sodium-2-ethylhexanoic acid (0.128 g, 0.75 mmol) in ethyl acetate (15 mL) was added. The resulting precipitate was filtered and purified by preparative liquid chromatography (C-18 reverse phase, 0–50% aqueous acetonitrile gradient) to give the desired product as a white lyophilized powder (56 mg, 31% yield).

EXAMPLE 30

(S)-1-Ethyl-6-fluoro-1,4-dihydro-4-oxo-7-[4-[[(1-sulfo-2-oxo-3-azetidinyl)-imino]methyl]-1-piperazinyl]-3-quinoline carboxylic acid disodium salt

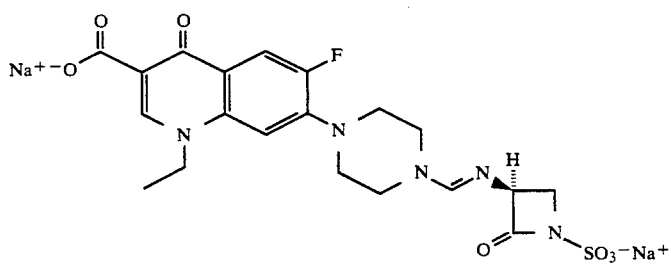

EXAMPLE 29

[2R-(2α,5α,6β)]-7-[4-[[(2-Carboxy-3,3-dimethyl-7-oxo-4-thia-1-azabicyclo[3.2.0]hept-6-yl)amino]methylene]-1-piperazinyl]-6,8-difluoro-1-(2-fluoroethyl)-1,4-dihydro-4-oxo-3-quinolinecarboxylic acid monosodium salt To a solution of the quinolone dimethylacetaltetrabutylammonium salt (prepared as described in Example 15, but on a 0.5 mmol scale), in anhydrous dimethylformamide (4.0 mL) was added a solution of (S)-3-amino-2-oxo-azetidine-1-sulfonic acid [*J. Org. Chem.*, 26, 5160 (1982)] (74.8 mg, 0.45 mmol) and diisopropylethylamine (78 μL, 0.45 mmol) in anhydrous dimethyl-

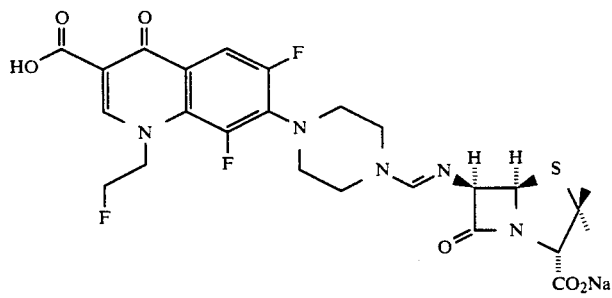

To a stirred suspension of the trifluoroquinolone from Example 28 (0.106 g, 0.3 mmol) in water (2.0 mL) was added aqueous sodium hydroxide (1N, 0.6 mL, 0.6 mmol). After a clear solution had been obtained, a solution of tetrabutylammonium hydrogen sulfate (0.101 g, 0.3 mmol) in water (2 mL) was added and the mixture was freeze dried. The freeze-dried material was stirred with dichloromethane (50 mL), filtered, and the solvent was removed to give the tetrabutylammonium salt. The salt was dissolved in methanol (10 mL), dimethylformamide (10 mL) was added, and the mixture was heated at reflux overnight. The solvent and excess reagent were removed under high vacuum to give the quinolone dimethylacetal as a pale yellow gum. The acetal was dissolved in anhydrous chloroform (8 mL) and added to a solution of 6-aminopenicillanic acid (65 mg, 0.3 mmol) and diisopropylethylamine (53 μL, 38.7 mg, 0.3 mmol) in chloroform (4 mL). The solution formamide (2.0 mL). The mixture was stirred at ambient temperature for 4 hours, and then a solution of sodium-2-ethylhexanoate (183 mg, 1.1 mmol) in ethylacetate (3 mL) was added. The resulting mixture was stirred at room temperature for 10 minutes and then dichloromethane (12 mL) was added. The sodium salt, which precipitated, was collected by filtration and washed with dichloromethane (3×4 mL). The crude mixture was purified by preparative liquid chromatography (C-18 reverse phase, 0–100% aqueous acetonitrile gradient) to give the product as a white amorphous powder after lyophilization (96 mg, 40% yield).

EXAMPLE 31

(2S-cis)-7-[4-[[[2-[[(Aminocarbonyl)oxy]methyl]-4-oxo-1-sulfo-3-azetidinyl]-imino]methyl]-1-piperazinyl]-1-ethyl-6-fluoro-1,4-dihydro-4-oxo-3-quinolinecarboxylic acid disodium salt

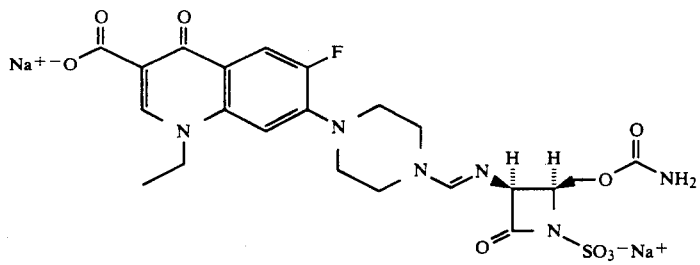

To a solution of the quinolone dimethylacetal prepared as described in Example 15 but on a 0.3 mmol scale, in anhydrous dimethylformamide (3.0 mL), was added a solution of (3S,4S)-3-amino-4-[(carbamoyloxy)-methyl]-2-oxo-azetidine-1-sulfonic acid [J. Org. Chem., 50, 3462 (1985)], (64.6 mg, 0.27 mmol) and diisopropylethylamine (47 µL, 0.27 mmol) in anhydrous dimethylformamide (2.0 mL). After the mixture had been stirred at ambient temperature for 4 hours, a solution of sodium-2-ethylhexanoic acid (100 mg, 0.6 mmol) in ethylacetate (2 mL) was added. The mixture was stirred for a further 10 minutes and then dichloromethane (10 mL) was added to precipitate the product as the disodium salt. The precipitate was collected by filtration, washed with dichloromethane (3×4 mL), and purified by preparative liquid chromatography (C-18 reverse phase, 0-100% aqueous acetonitrile), to give the product as a white lyophilized solid (90 mg, 54% yield).

EXAMPLE 32

[6R-[6α,7β(Z)]]-7-[4-[[[2-Carboxy-3-[[(1,2,5,6-tetrahydro-2-methyl-5,6-dioxo-1,2,4-triazin-3-yl)thio]methyl]-8-oxo-5-thia-1-azabicyclo[4.2.0]oct-2-en-7-yl]-imino]methyl]-1-piperazinyl]-1-ethyl-6-fluoro-1,4-dihydro-4-oxo-3-quinolinecarboxylic acid disodium salt

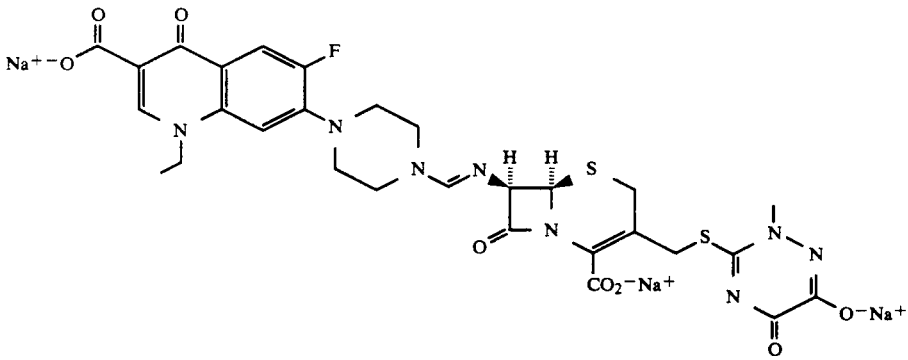

To a solution of the quinolone dimethylacetal (prepared as previously described in Example 15, 0.5 mmol) in anhydrous dimethylformamide (4.0 mL) was added a solution of (6R-trans)-7-amino-8-oxo-3-[[(1,2,5,6-tetrahydro-2-methyl-5,6-dioxo-1,2,4-triazin-3-yl)thio]methyl]-5-thia-1-azabicyclo[4,2,0]oct-2-ene-2-carboxylic acid (Eur. Pat. Appl. EP 65, 748) (167 mg, 0.45 mmol) and diisopropylethylamine (154 µL, 0.9 mmol) in anhydrous dimethylformamide. The mixture was stirred at room temperature for 4 hours and then a solution of sodium-2-ethylhexanoic acid (255 mg, 1.5 mmol) in ethyl acetate (5 mL) was added. The mixture was stirred for a further 10 minutes, dichloromethane (15 mL) was added, and the resulting precipitate was filtered and washed with dichloromethane (3×4 mL). The crude product was purified by preparative liquid chromatography (C-18; reverse phase, 0-100% aqueous acetonitrile gradient), to give the desired product as a white crystalline solid after lyophilization (25 mg, 8% yield).

EXAMPLE 33

1-Ethyl-6-fluoro-1,4-dihydro-7-(hexahydro-1H-1,4-diazepin-1-yl)-4-oxo-3-quinolinecarboxylic acid (Homonorfloxacin).

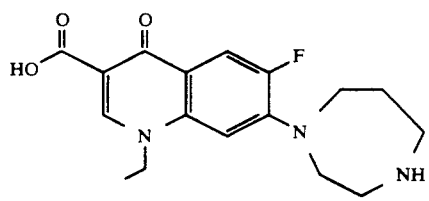

A mixture of 7-chloro-1-ethyl-6-fluoro-1,4-dihydro-4-oxo-3-quinolinecarboxylic acid [J. Med. Chem., 23, 1358 (1980)] (2.7 g, 10 mmol) and homopiperzine, (5.0 g, 50 mmol) was heated at 140° C. for 5½ hours. The excess homopiperazine was removed by distillation at 85°-95° C./10 mm Hg. The residue was triturated with water and filtered. The solid collected was dissolved in glacial acetic acid (1.5 mL), water (10 mL) was added, and the pH was adjusted to 8.0 with solid sodium bicarbonate. The resulting precipitate was collected by filtration, washed with water (3×5 mL) and air dried to give the product as a white crystalline solid (1.34 g, 40% yield): mp 196°-198° C.

EXAMPLE 34

[2s-(2α,5α,6β)]-7-[4-[[(2-Carboxy-3,3-dimethyl-7-oxo-4-thia-1-azabicyclo[3.2.0]hept-yl)imino]methyl]-hexahydro-1H, 1,4-diazepin-1-yl]-1-ethyl-6-fluoro-1,4-dihydro-4-oxo-3-quinolone carboxylic acid disodium salt

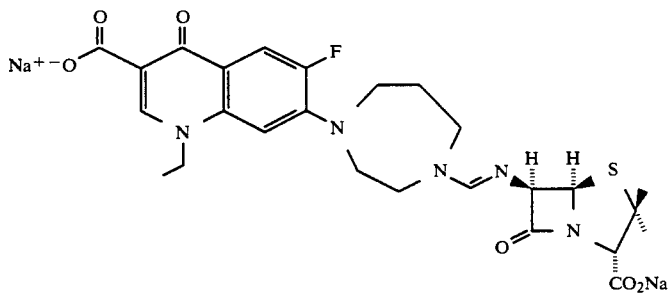

The tetrabutyl ammonium salt of homonorfloxacin (from Example 33) was prepared and converted into the dimethylacetal by the procedure used for the corresponding norfloxacin analog (on a 0.3 mmol scale). This was coupled to 6-aminopenicillanic acid (58.3 mg, 0.27 mmol) by following the procedure as described for the synthesis of the product in Example 16. Purification by preparative liquid chromatography (C-18 reverse phase, 0-100% aqueous acetonitrile gradient) gave the produce as a white lyophilized powder (41.3 mg, 25% yield).

EXAMPLE 35

[2s-(2α,5α,6β)-7-[4-[[(2-Carboxy-3,3-dimethyl-7-oxo-4-thia-1-azabicyclo[3.2.0]-hept-6-yl)imino]methyl]-1-piperazinyl]-1-ethyl-6-fluoro-1,4-dihydro-4-oxo-1,8-naphthyridine-3-carboxylic acid disodium salt

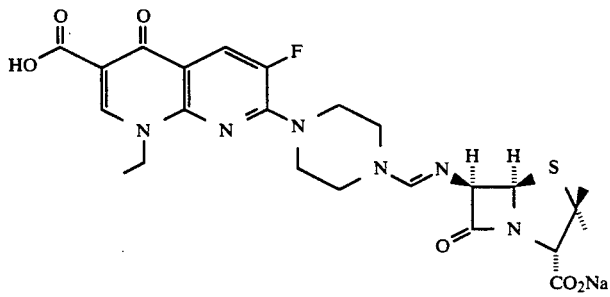

The tetrabutyl ammonium salt of enoxacin [*J. Med. Chem.*, 27, 292 (1984)] was prepared and converted into the corresponding dimethylacetal, using the procedure described for the corresponding norfloxacin analog in Example 15 (but done on a 0.112 mmol scale). This was coupled to 6-aminopenicillanic acid (24. 2 mg, 0.112 mmol) by following the procedure as described for the preparation of the product in Example 33. The product, which was very unstable, was purified by preparative liquid chromatography (C-18 reverse phase, 0-100% aqueous acetonitrile gradient) to give an amorphous, pale yellow powder after lyophilization (16.4 mg, 25% yield).

EXAMPLE 36

[2s-(2α,5α,6β)]-7-[4-[[(2-Carboxy-3,3-dimethyl-7-oxo-4-thia-1-azabicyclo[3.2.0]hept-6-yl)imino]methyl]hexahydro-1H-1,4-diazepin-1-yl]-1-ethyl-6-fluoro-1,4-dihydro-4-oxo-1,8-naphthyridine-3-carboxylic acid disodium salt

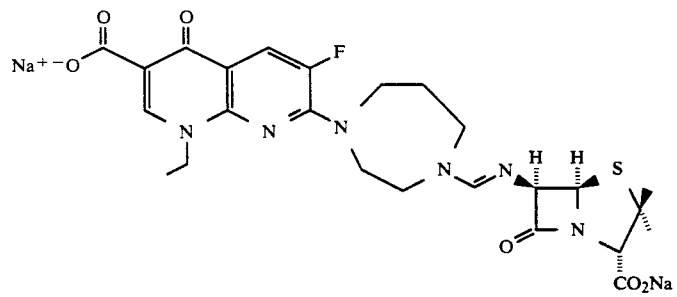

The tetrabutylammonium salt of homoenoxacin [*J. Med. Chem.*, 27, 292 (1984)] was prepared and converted into the dimethylacetal derivative in an analogous manner to the procedure described in Example 15 (except on a 0.277 mmol scale). This was coupled with 6-aminopenicillanic acid (60 mg, 0.277 mmol) as described for the preparation of the product in Example 33. Purification by preparative liquid chromatography (C-18 reverse phase, 0-100%, aqueous acetonitrile gradient) gave the product as a pale yellow amorphous solid after lyophilization (30 mg, 18% yield).

We claim:
1. A compound of formula

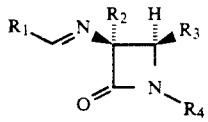

wherein $R_1$ is a cyclic or secondary acyclic amino group which independently has antibacterial activity selected from the group consisting of

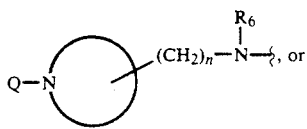

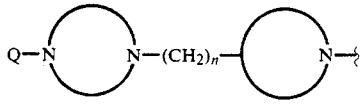

in which

represents a 5-, 6-, or 7-membered substituted or unsubstituted heterocycle having one or more heteroatoms selected from the group consisting of nitrogen, oxygen, and sulfur;

represents a 5- or 6-membered substituted or unsubstituted heterocycle having one or two heteroatoms selected from the group consisting of nitrogen, oxygen, and sulfur; Q represents a substituted quinolinyl or naphthyridinyl group; $R_6$ is lower alkyl or lower alkyl substituted with one or more azido, amino, halogen, hydroxy, carboxy, cyano, alkoxycarbonyl, aminocarbonyl, alkanoyloxy, alkoxy, ayloxy, mercapto, alkylthio, aylthio, alkylsulfinyl, or alkylsulfonyl groups; n is zero, 1, or 2; and
$R_2$ is hydrogen, lower alkoxy, lower alkylthio, or formamide;

represents

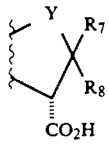

in which Y is S; and
$R_7$ and $R_8$ are independently hydrogen or lower alkyl; or a readily hydrolyzable ester or pharmaceutically acceptable salt of the compound, or a hydrogen of any of the foregoing.

2. A compound as in claim 1, in which $R_1$ is of the formula

in which

represents a 5-, 6- or 7-membered substituted or unsubstituted ring, and Q is a substituted quinolinyl or naphthyridinyl group.

3. A compound as in claim 2, in which $R_1$ is a substituted piperazinyl group of the formula

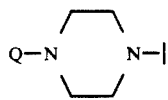

in which Q is a substituted quinolinyl or naphthyridinyl group.

4. A compound as in claim 2, in which $R_1$ is a substituted piperazinyl group of the formula

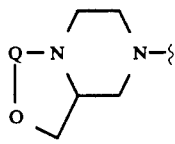

in which Q is a substituted quinolinyl or naphthyridinyl group.

5. A compound as in claim 2, in which $R_1$ is a substituted diazepinyl group of the formula

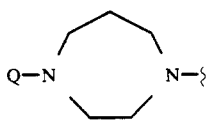

in which Q is a substituted quinolinyl or naphthyridinyl group.

6. A compound as in claim 1, in which $R_1$ is of the formula

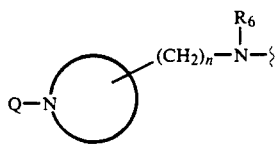

in which

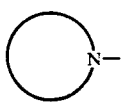

represents a 5- or 6-membered substituted or unsubstituted heterocycle, $r_6$ is lower alkyl or substituted lower alkyl, Q represents a substituted quinolinyl or naphthyridinyl group, and n is zero, 1 or 2.

7. A compound as in claim 6, in which $R_1$ is a substituted pyrrolidinylamino group of the formula

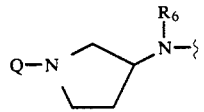

in which Q is a substituted quinolinyl or napthyridinyl group, and $R_6$ is lower alkyl or substituted lower alkyl.

8. A compound as in claim 1, in which $R_1$ is of the formula

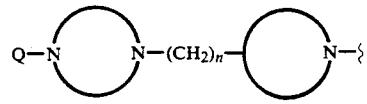

in which

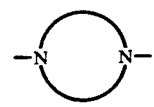

represents a 5-, 6- or 7-membered heterocycle which is substituted or unsubstituted, Q is a substituted quinolinyl or naphthyridinyl ring, and n is zero, 1 or 2.

9. A compound as in claim 7, in which $R_1$ is a substituted pyrrolidinylmethylamino group of the formula

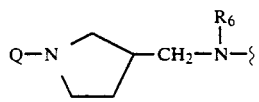

in which Q is a substituted quinolinyl or naphthyridinyl group and $R_6$ is lower alkyl or substituted lower alkyl.

10. A compound as in claim 1, which is of the formula

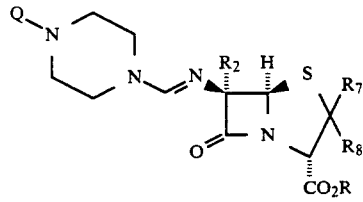

in which $R_2$ is hydrogen, lower alkoxy, lower alkylthio or formamide, Q is a substituted quinolinyl or naphthyridinyl group, $R_7$ and $R_8$ are independently hydrogen or lower alkyl, and R is hydrogen or a metal cation.

11. A compound as in claim 10, in which Q is of the formula

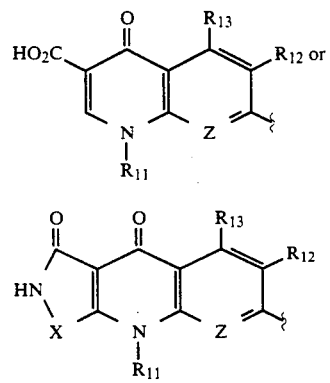

in which Z represents C—$R_{10}$ or N; X represents S or O; $R_{10}$ represents hydrogen, halogen or an oxymethylene (—$OCH_2$—) bridge to the piperazine nucleus to form a fused six-membered ring; alternatively, $R_{10}$ may be an oxymethylene bridge to the first atom of the N-substituent so as to form a fused six-membered ring; $R_{11}$ represents hydrogen, lower alkyl, lower alkenyl, $C_3$ to $C_7$ cycloalkyl, substituted lower alkyl (preferably halo substituted), or mono-, di-, or trihalophenyl; $R_{10}$ and $R_{11}$ when taken together represent lower alkylene of 3 to 5 carbon atoms, a lower alkylene mono-oxy group of 2 to 4 carbon atoms, or a group of the formula —$OCH_2N(CH_3)$—; $R_{12}$ is hydrogen or halogen; and $R_{13}$ is hydrogen or amino.

12. A compound as in claim 1, which is [2S-(2α,5α, 6β)]-6-[[[4-[1-ethyl-6-fluoro-1,4-dihydro-3-(methoxycarbonyl)-4-oxo-7-quinolinyl]-1-piperazinyl]methylene]amino]-3,3-dimethyl-6-oxo-4-thia-1-axzabicyclo[3.2.0]heptane-2-carboxylic acid, or a pharmaceutically acceptable salt thereof.

13. A compound as in claim 1, which is [2S-(2α,5α,6 β)]-7-[4-[[[2-(carboxy)-3,3-dimethyl-7-oxo-4-thia-1-azabicyclo[3.2.0]hept-6-yl]imino]methyl]-1-piperazinyl]-1-ethyl-6-fluoro-1,4-dihydro-4-oxo-3- quinolinecarboxylic acid, or a pharmaceutically acceptable salt thereof.

14. A compound as in claim 1, which is 2R-(2α,5α,6β)]-7-[4-[[(2-carboxy-3,3-dimethyl-7-oxo-4-thia-1-azabicyclo[3.2.0]hept-6-yl)amino]-methylene]-1-piperazinyl]-6,8-difluoro-1-(2-fluoroethyl)-1,4-dihydro-4-oxo-3-quinoline-carboxylic acid, or a pharmaceutically acceptable salt thereof.

15. A compound as in claim 1, which is [2S-(2α,5α,6β)]-7-[4-[[(2-carboxy-3,3-dimethyl-7-oxo-4-thia-1-azabicyclo[3.2.0]hept-6-yl)-imino]methyl]hexahydro-1H-1,4-diazepin-1-yl]-1-ethyl-6-fluoro-1,4-dihydro-4-oxo-3-quinolinecarboxylic acid, or a pharmaceutically acceptable salt thereof.

16. A compound as in claim 1, which is [2S-(2α,5α,6β]-7-[[[4-(2-carboxy-2,3-dimethyl-7-oxo-4-thia-1-azabicyclo[3.2.0]-hept-6-yl)imino]methyl]-1-piperazinyl]-1-ethyl-6-fluoro-1,4-dihydro-4-oxo-1,8-naphthyridine-carboxylic acid, or a pharmaceutically acceptable salt thereof.

17. A compound as in claim 1, which is [2S-(2α,5α,6β)]-7-[4-[[2-carboxy-3,3-dimethyl-7-oxo-4-thia-1-azabicyclo[3.2.0]hept-6-yl)-imino]methyl]hexahydro-1H-1,4-diazepin-1-yl]-1-ethyl-6-fluoro-1,4-dihydro-4-oxo-1,8-naphthyridine-carboxylic acid, or a pharmaceutically acceptable salt thereof.

* * * * *

UNITED STATES PATENT AND TRADEMARK OFFICE
CERTIFICATE OF CORRECTION

PATENT NO. : 5,159,077
DATED : October 27, 1992
INVENTOR(S) : Dennis Dalton Keith, et. al.

It is certified that error appears in the above-indentified patent and that said Letters Patent is hereby corrected as shown below:

Claim 1, column 43, lines 5-10, delete the chemical formula and replace with
--

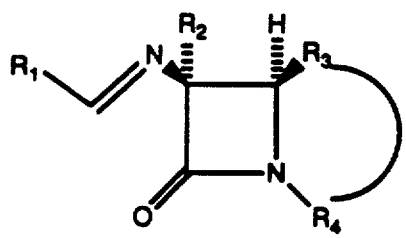   I

--.

Claim 3, column 44, lines 45-50, delete the chemical formula and replace with
--

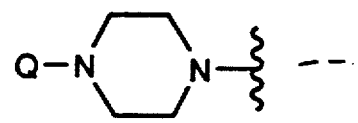 --

UNITED STATES PATENT AND TRADEMARK OFFICE
CERTIFICATE OF CORRECTION

PATENT NO. : 5,159,077

DATED : October 27, 1992

INVENTOR(S) : Dennis Dalton Keith, et. al.

It is certified that error appears in the above-indentified patent and that said Letters Patent is hereby corrected as shown below:

Claim 6, column 45, line 31, change "$r^6$" to -- $R^6$ --.

Claim 10, column 46, line 22, change "formamide" to -- formamido --.

Claim 12, column 46, line 62, change "axzabicy-" to -- azabicy- --.

Claim 12, column 46, line 63, change "pharmaceti-" to -- pharmaceuti- --.

Claim 16, column 48, line 4, change " 4-(2" to -- [4-[[(2 --.

Signed and Sealed this

Eleventh Day of January, 1994

Attest:

BRUCE LEHMAN

Attesting Officer

Commissioner of Patents and Trademarks